United States Patent
Schroth et al.

(10) Patent No.: US 9,492,075 B2
(45) Date of Patent: Nov. 15, 2016

(54) PRISM PRESCRIPTION VALUE ACQUISITION SYSTEM, ACQUISITION METHOD, ACQUISITION APPARATUS AND PROGRAM FOR CORRECTING FIXATION DISPARITY

(71) Applicant: HOYA CORPORATION, Tokyo (JP)

(72) Inventors: Volkhard Schroth, Freiburg (DE); Wolfgang Jaschinski, Dortmund (DE); (Continued)

(73) Assignee: HOYA CORPORATION, Tokyo (JP)

(*) Notice: Subject to any disclaimer, the term of this patent is extended or adjusted under 35 U.S.C. 154(b) by 0 days.

(21) Appl. No.: 14/761,668

(22) PCT Filed: Jan. 20, 2014

(86) PCT No.: PCT/JP2014/050983
§ 371 (c)(1),
(2) Date: Aug. 19, 2015

(87) PCT Pub. No.: WO2014/112626
PCT Pub. Date: Jul. 24, 2014

(65) Prior Publication Data
US 2015/0351625 A1  Dec. 10, 2015

(30) Foreign Application Priority Data
Jan. 18, 2013  (DE) .................. 10 2013 100 516

(51) Int. Cl.
*A61B 3/08*  (2006.01)
*A61B 3/00*  (2006.01)

(52) U.S. Cl.
CPC .............. *A61B 3/08* (2013.01); *A61B 3/0025* (2013.01); *A61B 3/0091* (2013.01); *A61B 3/085* (2013.01)

(58) Field of Classification Search
USPC .................................................. 351/200–246
See application file for complete search history.

(56) References Cited

U.S. PATENT DOCUMENTS

| | | |
|---|---|---|
| 4,222,639 A | 9/1980 | Sheedy |
| 5,026,151 A | 6/1991 | Waltuck et al. |
| | (Continued) | |

FOREIGN PATENT DOCUMENTS

| | | |
|---|---|---|
| EP | 0512443 B1 | 1/1996 |
| JP | H08-164112 A | 6/1996 |
| | (Continued) | |

OTHER PUBLICATIONS

Apr. 22, 2014 International Search Report issued in International Patent Application No. PCT/JP2014/050983.
(Continued)

*Primary Examiner* — Mohammed Hasan
(74) *Attorney, Agent, or Firm* — Oliff PLC

(57) ABSTRACT

A prism prescription value acquisition system that includes a calculation part for numerically transforming a fixation disparity amount (unit: angle), which indicates a degree at which the visual axis is shifted from the central fovea of the retina when a subject conducts visual fixation of a target, into a prism prescription value by multiplying the fixation disparity amount by a coefficient when the fixation disparity amount is within ±4 minutes. Herein, the prism prescription value is calculated according to the following equation: $AP_{ver}=k_{ver}*FD_{ver}$, $AP_{hor}=k_{hor}*FD_{hor}$ providing that each of coefficients $k_{hor}$ and $k_{ver}$ satisfies the following conditions: $0.3 \le k_{ver} \le 0.7$, $1.4 \le k_{hor} \le 2.0$.

14 Claims, 15 Drawing Sheets

(72) Inventors: Hans Warntjes, Dronten (NL); Takashi Hatanaka, Higashimurayama (JP)

(56) References Cited

U.S. PATENT DOCUMENTS

| | | | |
|---|---|---|---|
| 5,331,358 | A | 7/1994 | Schurle et al. |
| 7,275,823 | B2 * | 10/2007 | Fukuma ................. A61B 3/103 351/205 |
| 7,597,445 | B2 | 10/2009 | Sakurada et al. |
| 2002/0176051 | A1 | 11/2002 | Saladin |
| 2005/0018132 | A1 | 1/2005 | Fukuma et al. |
| 2007/0229762 | A1 | 10/2007 | Sakurada et al. |

FOREIGN PATENT DOCUMENTS

| | | |
|---|---|---|
| JP | H11-155813 A | 6/1999 |
| JP | 2007-268157 A | 10/2007 |
| JP | 4302525 B2 | 7/2009 |

OTHER PUBLICATIONS

London et al; "Fixation disparity analysis: sensory and motor approaches;" Optometry; Dec. 2006; vol. 77; pp. 590-608.
Jul. 30, 2015 International Preliminary Report on Patentability issued in International Patent Application No. PCT/JP2014/050983.
Sep. 1, 2016 Search Report issued in European Patent Application No. 14741004.7.
Gray; "The Prescribing of Prisms in Clinical Practice;" Graefes Arch Clin Exp Ophthalmol; Apr. 2008; vol. 246; No. 5; pp. 627-629.

* cited by examiner (a)    (b)    (c)

(a)

(b)

(c)

(a)

(b)

61 Far distance: Determination of the vertical correction prism

62 Far distance: Determine the horizontal correction prism

63 Near distance: Determine the vertical correction prism

64 Near distance: Determine the horizontal correction prism

71 No prism: FD test 01 (vertical FD)

72 Far distance: Determine the vertical correction prism

73 Far distance: The test figure for horizontal FD is displayed. The subject adjusts the location by the touch pad.

76 Instruction to the examiner
: 1.0 prism base out

77 The examiner sets 1.0 prism base out

78 The subject adjusts the test figure again by the touch pad

ArcTAN(a) = d/VD d: Location of the vernier (shift amount) adjusted by the patient so that the vernier is perceived to be located at the center VD: Observation distance between the patient's eye to the visual target surface (a)

(b)

a = Is fixation disparity amount equal to or less than the predetermined value?

PRISM PRESCRIPTION VALUE ACQUISITION SYSTEM, ACQUISITION METHOD, ACQUISITION APPARATUS AND PROGRAM FOR CORRECTING FIXATION DISPARITY

TECHNICAL FIELD

The present invention relates to a prism prescription value acquisition system, acquisition method, acquisition apparatus and program for correcting fixation disparity, and more particularly to a prism prescription value acquisition system, acquisition method, acquisition apparatus and program for correcting fixation disparity of a subject by use of a spectacle lens.

BACKGROUND ART

When a person wears spectacle lenses, a variety of elements, such as far vision, near vision, and astigmatism are taken into account. These elements also include elements referred to as visual functions. These visual functions are, for example, functions related to strabismus, heterophoria, aniseikonia, and fixation disparity.

Fixation disparity is a phenomenon that when a target is binocularly viewed (visual fixation), an image of the target cannot be formed at the location of the central fovea of the retina in either one or both eyes, but an image is formed at a location slightly deviated from the central fovea. In other words, fixation disparity is a phenomenon that at the time of the visual fixation of a target, the visual line of either one or both eyes is directed to the direction slightly deviated from the direction of the target.

In the case of a person who has normal stereoscopic visual acuity, if the degree of misalignment of the visual line due to fixation disparity is within a Panum's area, images that have been formed each at a location slightly deviated from the central fovea of the right and left retinas can be perceived as one image by means of processing by the brain, referred to as fusion, thereby enabling stereoscopic vision. For this reason, a person who has fixation disparity is not aware of it and it is also difficult for the person to be aware that vision is impaired. Since density of visual cells rapidly decreases at a location even slightly distant from the central fovea, fine visual acuity cannot be acquired at the location. Therefore, the person with fixation disparity whose visual lines of right and left eye are slightly deviated from the central fovea of right and left retinas due to fixation disparity has decreased visual acuity and perceives a blurred image. Even when an image is blurred only to one eye, the image viewed by the other eye is clear when viewed binocularly; therefore, the person is seldom aware of having deteriorated visual acuity. Accordingly, there are many cases in which constriction of the visual field, eyestrain, headache, stiff shoulder, dizziness, etc. develop without subjective symptoms in addition to a decrease in visual acuity which is a symptom of fixation disparity.

A well-known method of examining the presence or absence of fixation disparity and the degree of fixation disparity is described in patent document 1 (specifically, FIG. 5(b) and FIGS. 6 to 8 in particular). The method described in patent document 1 is as follows:

For example, while a visual target (sign 50) for fixing each visual line of both eyes is displayed on the display unit as a common visual target to both right and left eyes, only the upper visual target (sign 43) is presented to the right eye, and only the lower visual target (sign 45) is presented to the left eye. At this time, on the display unit, both visual targets (43, 45) are displayed at locations that are vertically aligned. However, when both visual targets (43, 45) are presented to a subject who has fixation disparity, the subject perceives both visual targets (43, 45) as being out of alignment as shown in FIG. 6. Then, the subject moves the upper visual target (43) by means of the operating portion, thereby moving the two visual targets (44, 45) so that the subject can perceive both the visual targets (43, 45) as being displayed at locations that are aligned. By doing so, the subject can perceive both visual targets (43, 45) as being aligned. On the other hand, on the display unit, or the real space, since both visual targets (43, 45) have been moved by the subject, both the targets are displayed at locations that are out of alignment with each other. The shift amount (i.e., shift amount in the right and left directions) of both visual targets (43, 45) on the aforementioned display unit corresponds to the fixation disparity amount. Accordingly, the right and left direction (horizontal direction) fixation disparity amount can be obtained. In the same manner, by using the left-side visual target (sign 44) presented only to the left eye and the right-side visual target (sign 45) presented only to the right eye, it is possible to obtain a fixation disparity amount in the vertical direction (top and bottom direction).

Generally, to eliminate the fixation disparity, the spectacles which is prescribed the prisms to cancel the fixation disparity is usually worn by the patient. By wearing the spectacles with the prescribed prisms, many of patients who have fixation disparity will be able to see objects without fixation disparity. Their visual lines of both eyes will be turned for correct directions.

Conventionally, in order to detect a prism amount necessary for eliminating fixation disparity, a subject wore a trial lens provided with a prism, and measurement to check the presence or absence of fixation disparity was repeatedly carried out until a trial lens that helps eliminate the fixation disparity was found. Then, the amount of prism and its base direction of the detected trial lens was used as a prism prescription value.

Thus, the amount of prism and its base direction which has been obtained as the result of trial and error by use of a trial lens or the like and which eliminates fixation disparity when the spectacle lens is worn is referred to as an "aligning prism". The aligning prism is also a prism prescription value finally provided for a spectacle lens.

Back to patent document 1, it does not describe a method of obtaining an aligning prism. Therefore, even if fixation disparity is measured by the electrical means as shown in the method described in patent document 1, after all, an aligning prism will end up being obtained by adopting a method that uses a trial lens as stated above. That is, a subject wears a trial lens provided with a prism, and measurement is repeatedly conducted until a proper trial lens provided with a prism is found so that the subject can perceive both a pair of visual targets (43, 45) or (44, 45), displayed at locations that are aligned on the real-space display unit, as being located at locations that are aligned.

Furthermore, recently, it has been made clear that there is more than a simple relationship between the fixation disparity amount and the aligning prism, and the relationship significantly varies depending on the subject itself. That is, it has been made sure that even if the fixation disparity amount is the same, the prism amount (aligning prism) necessary for eliminating fixation disparity varies among different individuals (refer to FIG. 8 and FIG. 9 of non-patent document 1).

CITATION LIST

Patent Document

[Patent Document 1] U.S. Pat. No. 5,026,151

Non-Patent Document

[Non-Patent Document 1] "Richard London etc.)", "Fixation disparity analysis: Sensory and motor approaches", Optometry, Vol. 77, No. 12, December 2006, pp. 590-608"

SUMMARY OF INVENTION

Technical Problem

From non-patent document 1, the inventor has acquired findings that even if a fixation disparity amount is simply converted to prism diopter based on the distance between visual targets and a subject, the amount will not become an aligning prism to be eventually provided for a spectacle lens. This leads to the fact that since the relationship between the "prism amount converted from a fixation disparity amount based on the distance between visual targets and a subject" and the "aligning prism" significantly varies among different individuals, it is not possible to obtain an accurate aligning prism from the fixation disparity amount by means of calculation. If so, after all, even if a fixation disparity amount is obtained, there is no way to utilize it, and as in the same manner as the conventional method, to find a prism amount necessary for eliminating fixation disparity, there is no other way than painstakingly obtaining an aligning prism by use of a trial lens.

In the application that serves as a basis for priority rights (German Patent Application 102013100516.0), the following method, referred to as an "expert system", is implemented which uses the fixation disparity amount to obtain an aligning prism as described below. Herein, the following is a simplified description and details will be described later.

That is, based on the fixation disparity amount, software (hereinafter, software sometimes means a program) of the expert system issues instructions to an examiner as to a trial lens having a prism amount to be used next. Then, a subject wears the trial lens, and fixation disparity measurement will be conducted again. If fixation disparity is still recognized, another fixation disparity measurement is conducted by using another trial lens having a different prism amount. Thus, according to the description, the trial prism lens is kept being changed until fixation disparity is not recognized.

Surely, by this method, all that is required is to select a trial lens according to the instruction issued from the software and conduct the measurement procedure according to the instruction from the software, which makes it easier for an examiner to conduct measurement when compared to the conventional method that obtains an aligning prism. As a result, it is possible to efficiently obtain an aligning prism that can eliminate fixation disparity.

However, even in this method, it is difficult to avoid trial and error to find an aligning prism and it is also difficult to avoid using a trial lens.

When obtaining an aligning prism by use of a trial lens, the only known method is that a subject sequentially wears a plurality of trial lenses provided with a prism (e.g., 0.25 prism diopter increments, hereinafter referred to as "Δ"), and when the subject perceives visual targets, which are displayed individually to right and left eyes, as being located at locations that are aligned, the prism prescription value of the trial lens at that time is adopted. To use this method, each eyeglass shop has to prepare a large variety of trial lenses. Obviously, it takes time to have each subject wear a variety of trial lenses. Also, when trial lenses are prepared with 0.25Δ increments, if, for example, a subject needs a trial lens having a prism prescription value of 0.35Δ, it is not possible to provide an appropriate spectacle lens for the subject; consequently, the subject's fixation disparity cannot be corrected by means of a spectacle lens.

A spectacle user who has fixation disparity is hoping that the fixation disparity will be eliminated as the result of the measurement and prescription. None the less, the measurement means for obtaining an aligning prism to eliminate fixation disparity is complicated and measurement takes time. Therefore, in reality, only some optometrists, ophthalmologists, and eyeglass shops conduct this measurement, and fixation disparity has not been measured and prescribed generally.

Accordingly, a main objective of the present invention is to acquire a prism prescription value necessary for correcting fixation disparity by means of a spectacle lens in a simple, quick, and accurate manner.

Solution to Problem

To solve the aforementioned problem, the inventor devoted themselves to study. The inventor investigated the relationship between the "fixation disparity amount" and the "aligning prism". From the description in non-patent document 1, the relationship seems to significantly depend on the difference among individuals. However, after the inventor continuously investigated, the inventor found a fixed relationship between those two amounts and obtained the following findings. By taking advantage of the relationship, it is possible to calculate, from a fixation disparity amount, a prism amount necessary for eliminating the fixation disparity; that is, by the calculation using a fixation disparity amount within a limited range, it is possible to obtain an aligning prism which has been considered impossible to be calculated from the fixation disparity amount; that is, the fixation disparity amount can be converted to an aligning prism by means of calculation.

Specific embodiments devised based on the aforementioned findings are as follows.

A first embodiment in accordance with the present invention provides a prism prescription value acquisition system comprising:

a calculation part for numerically transforming a fixation disparity amount (unit: angle), which indicates a degree at which the visual axis is shifted from the central fovea of the retina when a subject conducts visual fixation of a target, into a prism prescription value by multiplying the fixation disparity amount by a coefficient when the fixation disparity amount is within ±4 minutes.

Herein, the prism prescription value is calculated according to the following equation:

$$AP_{ver} = k_{ver} * FD_{ver}$$

$$AP_{hor} = k_{hor} * FD_{hor}$$

$AP_{ver}$ represents a prism amount (unit: prism diopter) in the vertical direction (top and bottom direction) in the prism prescription value, $AP_{hor}$ represents a prism amount in the horizontal direction in the prism prescription value, and $FD_{ver}$ represents a fixation disparity amount in the vertical direction.

$FD_{hor}$ represents a fixation disparity amount in the horizontal direction, providing that each of coefficients $k_{hor}$ and $k_{ver}$ satisfies the following conditions:

$$0.3 \leq k_{ver} \leq 0.7$$

$$1.4 \leq k_{hor} \leq 2.0$$

A second embodiment in accordance with the present invention provides a prism prescription value acquisition system according to embodiment 1, further comprising a judgment part for judging whether the fixation disparity amount is within ±4 minutes or not, wherein when the judgment part judges that the fixation disparity amount is within ±4 minutes, the calculation part numerically transforms the fixation disparity amount into a prism prescription value.

A third embodiment in accordance with the present invention provides a prism prescription value acquisition system according to embodiment 1 or 2, further comprising:

a measuring part for measuring a fixation disparity amount, and a transmission part for transmitting the fixation disparity amount measured by the measuring part to the calculation part;

the measuring part comprising a display means for displaying, after setting the direction of fixation disparity, a visual target for the right eye presented only to the right eye, a visual target for the left eye presented only to the left eye, and a visual target for visual fixation for which a subject conducts visual fixation, and an input means for flexibly moving at least either the visual target for the right eye or the visual target for the left eye displayed on the display means, wherein when the visual target for the right eye or the visual target for the left eye is moved, the visual target for visual fixation is not moved, and in the state in which a subject continuously conducts visual fixation of the visual target for visual fixation, a fixation disparity amount is measured from a shift amount of the two visual targets on the display means.

A fourth embodiment in accordance with the present invention provides a prism prescription value acquisition system according to embodiment 3, wherein the visual target for the right eye (presented only to the right eye), the visual target for the left eye presented only to the left eye, and the visual target for visual fixation for which a subject conducts visual fixation displayed on the display means are included in one test figure, and the test figure can be flexibly placed at any location at the front of the background image provided with a plurality of visual targets for visual fixation.

A fifth embodiment in accordance with the present invention provides a prism prescription value acquisition system according to embodiment 3 or 4, wherein the display means is a stereoscopic image display means capable of presenting different images to the right eye and the left eye separately; the visual target for the right eye is presented to the subject's right eye and the visual target for the left eye is presented to the subject's left eye.

A sixth embodiment in accordance with the present invention provides a prism prescription value acquisition method for numerically transforming a fixation disparity amount (unit: angle), which indicates a degree at which the visual axis is shifted from the central fovea of the retina when a subject conducts visual fixation of a target, into a prism prescription value by multiplying the fixation disparity amount by a coefficient when the fixation disparity amount is within ±4 minutes.

Herein, the prism prescription value is calculated according to the following equation:

$$AP_{ver} = k_{ver} * FD_{ver}$$

$$AP_{hor} = k_{hor} * FD_{hor}$$

$AP_{ver}$ represents a prism amount (unit: prism diopter) in the vertical direction (top and bottom direction) in the prism prescription value, $AP_{hor}$ represents a prism amount in the horizontal direction in the prism prescription value, and $FD_{ver}$ represents a fixation disparity amount in the vertical direction.

$FD_{hor}$ represents a fixation disparity amount in the horizontal direction, providing that each of coefficients $k_{hor}$ and $k_{ver}$ satisfies the following conditions:

$$0.3 \leq k_{ver} \leq 0.7$$

$$1.4 \leq k_{hor} \leq 2.0$$

A seventh embodiment in accordance with the present invention provides a prism prescription value acquisition method according to embodiment 6, wherein whether a fixation disparity amount obtained by measurement A of the fixation disparity amount is equal to or less than a predetermined angle is judged, and when it is judged that the fixation disparity amount is equal to or less than the predetermined angle, the fixation disparity amount is numerically transformed into a prism prescription value, and when it is judged that the fixation disparity amount is more than the predetermined angle, the subject wears measurement spectacles provided with a predetermined prism amount suitable for the fixation disparity amount and measurement B of the fixation disparity amount is conducted again, then, any one of the following processes 1 to 3 is conducted.

(Process 1) When fixation disparity has ceased to be perceived in measurement B, the prism amount of the measurement spectacles is used as a prism prescription value.

(Process 2) When the subject still perceives fixation disparity even in measurement B and when in measurement B, eso fixation disparity is turned to exo fixation disparity, or exo fixation disparity is turned to eso fixation disparity, any one of the following processes (i) to (iv) is conducted.

(i) In measurement A, when the subject doesn't wear measurement spectacles provided with a predetermined prism amount, half of prism value of the measurement spectacles in measurement B is used as a prism prescription value.

(ii) In measurement A, when the subject wears measurement spectacles provided with a predetermined prism amount, the average value of the prism amount of the measurement spectacles in measurement A and the prism amount of the measurement spectacles in measurement B is used as a prism prescription value.

(iii) In measurement A, when the subject doesn't wear measurement spectacles provided with a predetermined prism amount, prism prescription value is calculated by following formula.

$$AP = P2 - P2 \times FD2/(FD2 - FD1)$$

(iv) In measurement A, when the subject wears measurement spectacles provided with a predetermined prism amount, prism prescription value is calculated by following formula.

$$AP = P2 - (P2 - P1) \ast FD2/(FD2 - FD1)$$

AP represents a prism amount (unit: prism diopter) in the prism prescription value.

FD1 and FD2 are the fixation disparity amounts before and after eso fixation disparity has been turned to exo fixation disparity, or exo fixation disparity has been turned to eso fixation disparity in measurement B.

The sign of FD1 and FD2 is such that it is positive when the direction of fixation disparity is outward and negative when it is inward.

P1 and P2 are the prism amounts provided before and after eso fixation disparity has been turned to exo fixation disparity, or exo fixation disparity has been turned to eso fixation disparity in measurement B.

(Process 3) When the subject still perceives fixation disparity even in measurement B and when in measurement B, either eso fixation disparity or exo fixation disparity remains, the subject wears measurement spectacles provided with a higher power prism than the predetermined prism amount, and the fixation disparity amount is measured again, then the measurement of the fixation disparity amount is repeatedly conducted by increasing the power of the prism provided for the measurement spectacles until the state of (process 1) or (process 2) is achieved.

An eighth embodiment in accordance with the present invention provides a prism prescription value acquisition apparatus comprising:

a calculation part for numerically transforming a fixation disparity amount (unit: angle), which indicates a degree at which the visual axis is shifted from the central fovea of the retina when a subject conducts visual fixation of a target, into a prism prescription value by multiplying the fixation disparity amount by a coefficient when the fixation disparity amount is within ±4 minutes.

Herein, the prism prescription value is calculated according to the following equation:

$$AP_{ver} = k_{ver} \ast FD_{ver}$$

$$AP_{hor} = k_{hor} \ast FD_{hor}$$

$AP_{ver}$ represents a prism amount (unit: prism diopter) in the vertical direction (top and bottom direction) in the prism prescription value, $AP_{hor}$ represents a prism amount in the horizontal direction in the prism prescription value, and $FD_{ver}$ represents a fixation disparity amount in the vertical direction.

$FD_{hor}$ represents a fixation disparity amount in the horizontal direction, providing that each of coefficients $k_{hor}$ and $k_{ver}$ satisfies the following conditions:

$$0.3 \le k_{ver} \le 0.7$$

$$1.4 \le k_{hor} \le 2.0$$

A ninth embodiment in accordance with the present invention provides a prism prescription value acquisition program making a computer function as a calculation part for numerically transforming a fixation disparity amount (unit: angle), which indicates a degree at which the visual axis is shifted from the central fovea of the retina when a subject conducts visual fixation of a target, into a prism prescription value by multiplying the fixation disparity amount by a coefficient when the fixation disparity amount is within ±4 minutes.

Herein, the prism prescription value is calculated according to the following equation:

$$AP_{ver} = k_{ver} \ast FD_{ver}$$

$$AP_{hor} = k_{hor} \ast FD_{hor}$$

$AP_{ver}$ represents a prism amount (unit: prism diopter) in the vertical direction (top and bottom direction) in the prism prescription value, $AP_{hor}$ represents a prism amount in the horizontal direction in the prism prescription value, and $FD_{ver}$ represents a fixation disparity amount in the vertical direction.

$FD_{hor}$ represents a fixation disparity amount in the horizontal direction, providing that each of coefficients $k_{hor}$ and $k_{ver}$ satisfies the following conditions:

$$0.3 \le k_{ver} \le 0.7$$

$$1.4 \le k_{hor} \le 2.0$$

Advantageous Effects of Invention

According to the present invention, it is possible to acquire a prism prescription value necessary for correcting fixation disparity by means of a spectacle lens in a simple, quick, and accurate manner.

BRIEF DESCRIPTION OF DRAWINGS

FIG. 2(a) shows the situation where a subject who has eso fixation disparity perceives the test figure, FIG. 2(b) shows the situation where a subject who has no fixation disparity perceives the test figure, and FIG. 2(c) shows the situation where a subject who has exo fixation disparity perceives the test figure.

FIG. 3(a) is the test figure on the real space, when the subject who has Eso fixation disparity adjusted the position of nonius line 21 and 22 so that each lines can be seen as aligned by the subject. FIG. 3(b) is the test figure on the real space, when the subject who has no fixation disparity didn't adjust the position of nonius line 21 and 22. Each lines can be seen as aligned by the subject. FIG. 3(c) is the test figure on the real space, when the subject who has Exo fixation disparity adjusted the position of nonius line 21 and 22 so that each lines can be seen as aligned by the subject.

FIG. 5(a) shows a test figure for detecting fixation disparity in the vertical direction (top and bottom direction), and FIG. 5(b) shows a test figure for detecting fixation disparity in the horizontal direction.

FIG. 8 shows the situation where a test figure is placed at the front of the background image provided with a plurality of visual targets for visual fixation. FIG. 8(a) shows the situation where a test figure is displayed on the left side of the display means in the first measurement, and FIG. 8(b) shows the situation where a test figure is displayed on the right side of the display means in the second measurement.

FIG. 11(a) shows the situation where a subject cannot perceive the test figure (in the case of monocular observation), and FIG. 11(b) shows the situation where a subject can perceive the test figure.

DESCRIPTION OF EMBODIMENTS

Figure 1:
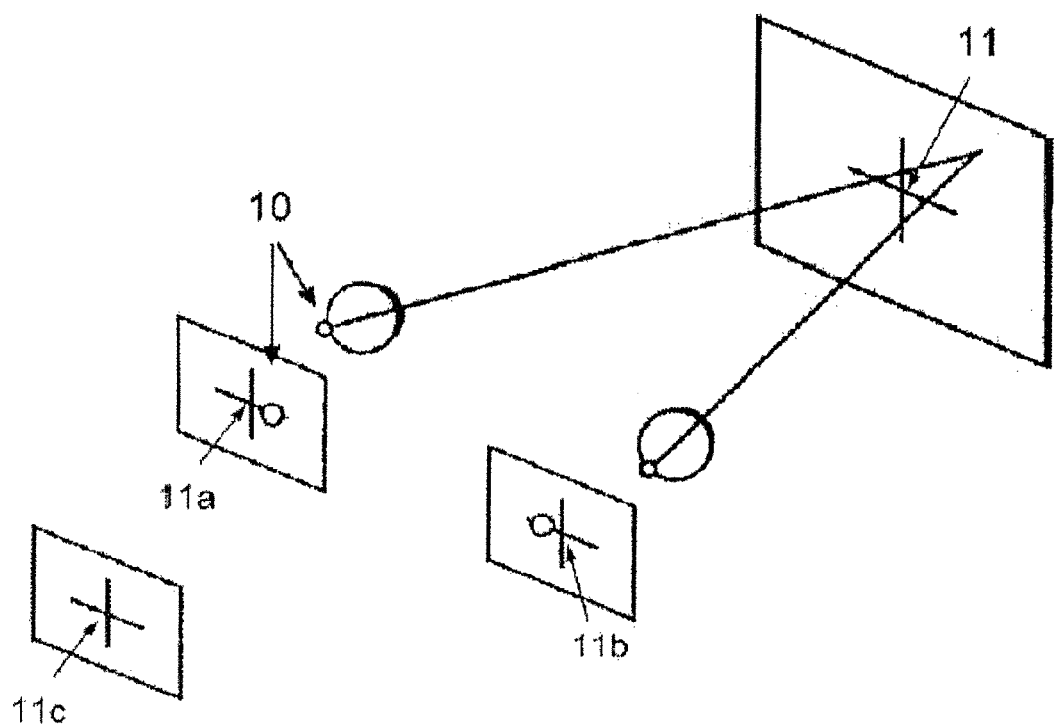
FIG. 1 shows a pair of eyes that are in the exo fixation disparity state.

Hereinafter, an embodiment of the present invention will be described according to the following sequential order:
1. Explanation of fixation disparity
2. Fixation disparity measurement mechanism in general terms
3. Conventional fixation disparity measurement method
4. Problems regarding fixation disparity measurement other than the problem to be solved by the present invention
5. Prism prescription value acquisition system
5-A) Order-placing computer
5-A-a) Measuring part
5-A-a1) Display means
5-A-a2) Accessory device (3D spectacles)
5-A-a3) Selection means
5-A-a4) Input means
5-A-b) Transmission part
5-B) Order-receiving computer
5-B-a) Calculation part
6. Prism prescription value acquisition apparatus
7. Prism prescription value acquisition program
8. Prism prescription value acquisition method
9. Advantageous effects of this embodiment
10. Modification examples It is assumed that this Specification describes all of the contents of the application that serves as a basis for priority rights (German Patent Application 102013100516.0).

1. Explanation of Fixation Disparity

To view the work screen with both eyes without a problem, the convergence angle formed by the binocular visual axes (visual lines) has to be accurately adjusted by the extraocular muscle. And, maximum spatial resolving power needs to be exhibited so that the image of the target point gazed on the screen, which is a fixation point, can be formed at a location in the same direction as the central fovea of both eyes, which is the location of the central retina. In that case, details of the target point can be perceived, and binocular retina images can be optimally overlapped in the brain. This is referred to as "homo-directionality". However, deviation from the homo-directionality is likely to occur in a person who has normal binocular vision (good fusion and good stereoscopic vision). This means that visual axes of both eyes sometimes intersect each other at a location several millimeters back (outward) or front (inward) of the fixation point on the retina.

At that time, the convergence angle formed by binocular visual axes is several minutes (angle) smaller (outward) or larger (inward) than the geometrically optimal convergence angle. If this kinetic convergence adjustment error remains within a certain level of allowable range (Panum's area), the error is compensated for by sensory fusion, which is neurophysiological processing in the brain, thereby preventing a double image from being perceived. Such a convergence error is traditionally referred to as "fixation disparity" and defined as the state of binocular single vision in which fixation points of both eyes are deviated each other within the Panum's area and an image is thus formed.

2. Fixation Disparity Measurement Mechanism in General Terms

FIG. 1 shows a pair of eyes that are in the exo fixation disparity state. In FIG. 1, in each eye, the fixation point 11 (center of the cross) is decentered from the center of the central small fovea 10 (small circle), forming an image with the fixation points 11a and 11b. However, due to sensory fusion, the viewer perceives the image as a single image 11c (i.e., not as a double image).

It has been proven that fixation disparity correlates with visual problems. It is important to determine the size of the fixation disparity. To detect fixation disparity, what is necessary is a test figure provided with a visual target that is presented only to a subject's right eye or left eye, for example, a visual target, like (nonius line). By use of such test figures, for the nonius lines which are displayed to right eye and left eye separately, sensory fusion of the above-mentioned visual target (nonius line) will never act, and the size of the fixation disparity can be determined by means of the shift amount of noninus lines.

Such a test figure 20 provided with nonius lines 21 and 22 to detect fixation disparity are shown in FIG. 2(a), FIG. 2(b) and FIG. 2(c). As shown in FIG. 2(a) and FIG. 2(c), nonius lines 21 and 22 can be moved in opposite directions from each other on the image plane of the test figure 20. By use of an appropriate accessory device 23, such as shutter spectacles (3D spectacles) or polarized spectacles, one of the two nonius lines is presented to one eye, and the other nonius line is presented to the other eye. In FIG. 2(a) to FIG. 2(c), the lower nonius line 22 is presented to the left eye, and the upper nonius line 21 is presented to the right eye.

To measure fixation disparity, several kinds of test figures 20 in which nonius lines 21 and 22 have been moved by different amounts are placed in front of a subject. Next, the subject selects a test figure in which the nonius lines 21 and 22 are perceived as being aligned vertically.

Figure 2:
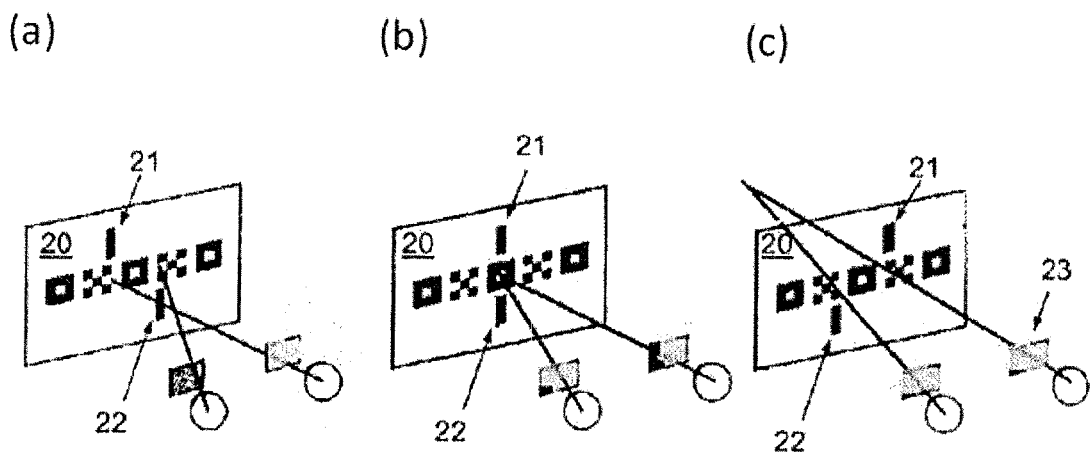
FIG. 2 shows test figures each provided with nonius lines to detect fixation disparity.
Figure 3:
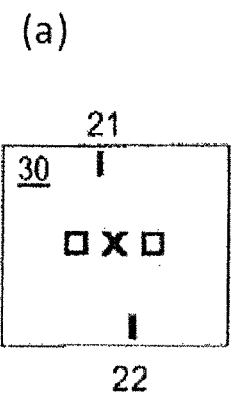
FIG. 3 shows different test figures that correspond to the test figures shown in FIG. 2, and each of those test figures also has nonius lines to detect fixation disparity.
Figure 3:
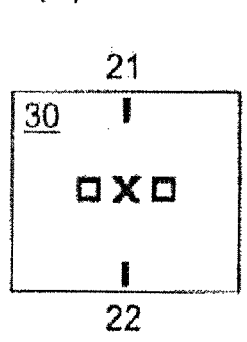
Figure 3:
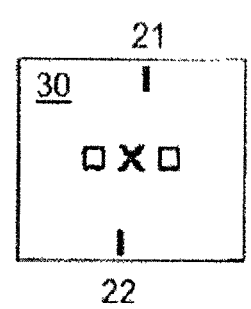

FIG. 2(a) shows the case of a subject who has eso fixation disparity where visual fixation lines intersect each other at the front of the test figure 20 (eso fixation disparity or eso FD). In this case, as shown in FIG. 2(a), visual fixation lines intersect each other at the front of the test figure 20. If that happens, although a subject tries to select a test figure in which the nonius line 21 and the lower nonius line 22 are perceived as being vertically aligned, the subject ends up selecting, in the real space, a test figure in which the upper nonius line 21 has been moved to the left and the lower nonius line 22 has been moved to the right as shown in FIG. 2(a). Furthermore, FIG. 3(a) shows a different test figures 30 in which the nonius lines 21 and 22 have been moved in corresponding ways. FIG. 3 shows different test figures that correspond to the test figures shown in FIG. 2, and each of the test figures in FIG. 3 has nonius lines to detect fixation disparity. FIG. 3(a) is the test figure on the real space, when the subject who has Eso fixation disparity adjusted the position of nonius line 21 and 22 so that each lines can be seen as aligned by the subject. FIG. 3(b) is the test figure on the real space, when the subject who has no fixation disparity didn't adjust the position of nonius line 21 and 22. Each lines can be seen as aligned by the subject. FIG. 3(c) is the test figure on the real space, when the subject who has Exo fixation disparity adjusted the position of nonius line 21 and 22 so that each lines can be seen as aligned by the subject.

In FIG. 2(b), visual fixation lines intersect each other on the plane of the test figure 20, which shows the case where a subject does not have fixation disparity. In this case, as shown in FIG. 2(b), when the subject sees the test figure 20 in which nonius lines 21 and 22 are located one above the other, the subject perceives those nonius lines 21 and 22 as being vertically aligned. In this case, some subjects select a test figure in which the upper nonius line 21 and the lower nonius line 22 are vertically aligned both perceptually and in the real space. FIG. 3(b) also shows a different test figure 30 in which nonius lines 21 and 22 are located one above the other.

Finally, in FIG. 2(c), visual fixation lines intersect each other at the back of the test figure 20, which shows the case where a subject has exo fixation disparity (exo fixation disparity or exo FD). As shown in FIG. 2(c), in this case, visual fixation lines intersect each other at the back of the test figure 20. If that happens, although a subject tries to select a test figure in which the nonius line 21 and the lower nonius line 22 are perceived as being vertically aligned, the subject ends up selecting, in the real space, a test figure in which the upper nonius line 21 has been moved to the right and the lower nonius line 22 has been moved to the left as shown in FIG. 2(c). Furthermore, FIG. 3(c) shows a different test figure 30 in which nonius lines 21 and 22 have been moved in corresponding ways.

Figure 5:
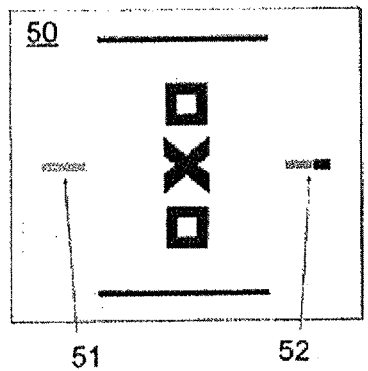
FIG. 5 shows test figures each provided with nonius lines to detect fixation disparity.
Figure 5:
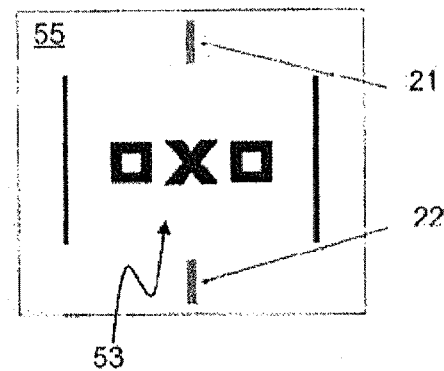

Similarly to the horizontal direction fixation disparity as shown in FIG. 2(a) and FIG. 2(c), vertical direction fixation disparity also exists. The test figure suitable for it is shown in FIG. 5(a). FIG. 5 shows test figures each provided with nonius lines to detect fixation disparity. FIG. 5(a) shows a test figure for detecting fixation disparity in the vertical direction (top and bottom direction), and FIG. 5(b) shows a test figure for detecting fixation disparity in the horizontal direction.

3. Conventional Fixation Disparity Measurement Method

Conventionally, a prism lens provided with prism power is normally used for a spectacle lens to correct fixation disparity.

Both horizontal and vertical fixation disparities can develop at the same time or either one can develop independently. At the time of optometry and examination in the department of ophthalmology, methods for determining a prism amount to correct fixation disparity have been used. However, those methods have a variety of disadvantages.

The components necessary for optometry include an apparatus to display at least a visual target, more than one test figure, and outline of the procedure for an examiner to make corrections by means of trial lenses.

The Mallett, Sheedy and Haase method has been used for several decades. In Britain, a so-called "Mallett unit" developed by Mallett has been used (Keeler Ltd., London). There are apparatuses for far vision (4 m) and apparatuses for near vision (40 cm). The test to determine a prism amount for correcting fixation disparity consists of a horizontally-oriented or vertically oriented nonius line and the mark "OXO" as a fusion target located at the center. As an improvement, the "Mallett double fixation disparity unit" for far vision has been devised.

In the U.S., the Sheedy fixation disparity meter was developed and is used specifically in the research field. This fixation disparity meter does not include fusion stimulants at the center and is designed to be used for tests that use the apparatus for near vision (40 cm) and the apparatus for far vision (4 m). Nonius lines provided with some predetermined deviation are displayed. By determining a prism value at which those lines are perceived as being aligned or by applying various different prism loads, it is possible to further analyze fixation disparity [Sheedy, James, E., U.S. Pat. No. 4,222,639, Sep. 16, 1980].

The invention described in U.S. Pat. No. 7,597,445 deals with examination of dissociative heterophoria (potential strabismus) in the measurement distance interacting with a subject and mainly uses a phoropter. However, adequacy of the invention for the examination of heterophoria is suspicious because measurement values are dispersed. Furthermore, the Sheared method used therein to determine a prism has disadvantages when compared with the FD method (Mallett, Sheedy, Haase).

In the German-speaking world, the "Polatest" visual function examination system developed by H. J. Haase around 1960 has been well-known. Principles of the visual function examination system are described in EP Patent No. 0512443B1 and U.S. Pat. No. 5,331,358A. This is a test apparatus for far vision (5 to 6 m) that uses polarization of the screen and polarized spectacles for subject.

A method of determining a prism amount to correct fixation disparity by using a polatest visual function examination system is described in some reports, and the International Binocular Vision Association edited those and published "Potential strabismus correction guidelines" (third edition, IVBV, June, 2005). This method has been significantly popular in the German-speaking world, though reliability of the method has not yet been proven scientifically. Furthermore, due to continuous improvements to this method, this method became even more complicated.

4. Problems Regarding Fixation Disparity Measurement Other than the Problem to be Solved by the Present Invention In addition to the "relationship between the fixation disparity amount and the aligning prism" described in the above "Technical Problem" to be solved by the present invention, the above-mentioned known methods have various problems. Some of those will be described below.

(1) The conventional subjective method to determine the aligning prism by means of trial lenses is based on verbal questions and answers intended to reveal subjective perception by a subject. Therefore, misperception could possibly cause errors.

(2) The conventional method uses a static visual condition where there is no visual line movement. Staring at an immobile target for a long time is not a natural visual condition, and test figures shown separately to both eyes (individually shown to the right eye and to the left eye) are often suppressed. Suppression indicates that a test figure to be judged becomes dim or disappears as the result of subjective perception, thereby judgment becomes very difficult or absolutely impossible.

(3) The two conventional methods cited above take time and are complicated. The method developed by Sheedy and the method developed by Haase each take at least 20 to 30 minutes. Moreover, those conventional methods require an examiner to have advanced knowledge; otherwise, the result might end up becoming useless.

(4) It is necessary to find beforehand micro strabismus for which correction by means of a prism is impossible (i.e., stereoscopic vision is unavailable), and examination of fixation disparity should not be provided for such a subject. Otherwise, the subject ends up receiving an unnecessary examination that results in useless measurements.

The configuration which has been devised to solve the aforementioned problems in addition to the problem to be solved by the present invention is this embodiment which will be described below.

5. Prism Prescription Value Acquisition System

Figure 13:
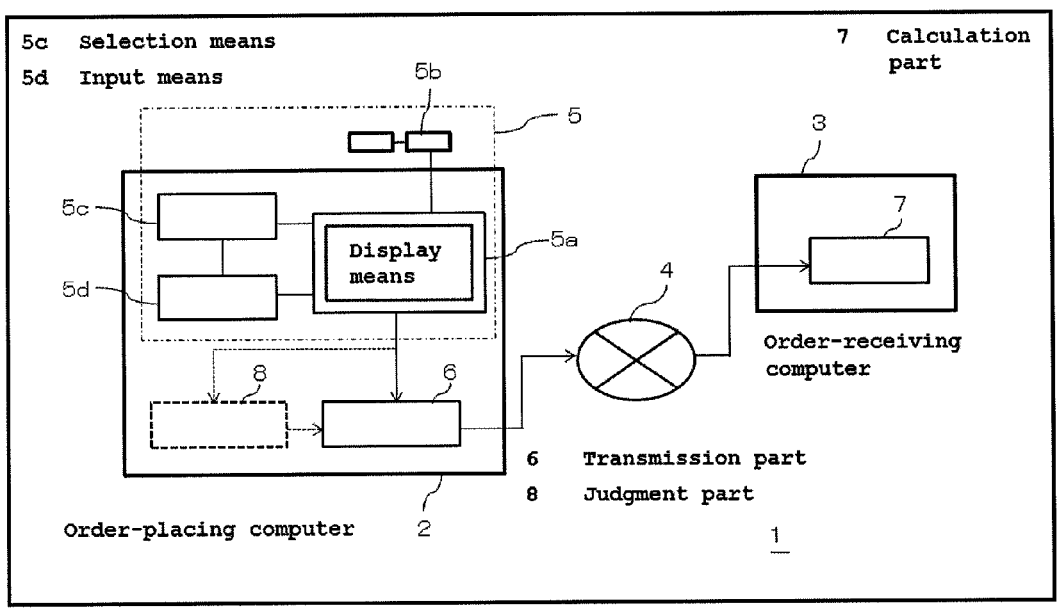
FIG. 13 is a schematic block diagram of the prism prescription value acquisition system according to this embodiment.

First, functional configuration of a prism prescription value acquisition system according to this embodiment will be described. FIG. 13 is a schematic block diagram of a prism prescription value acquisition system 1 according to this embodiment. The prism prescription value acquisition system 1 according to this embodiment is mainly provided with an order-placing computer 2 (also referred to as a "measurement-side computer") installed on the spectacle lens order placing side, and an order-receiving computer 3 (also referred to as a "calculation-side computer") installed on the spectacle lens order receiving side. The order-placing computer 2 and the order-receiving computer 3 are connected by a communication line 4.

Figure 9:
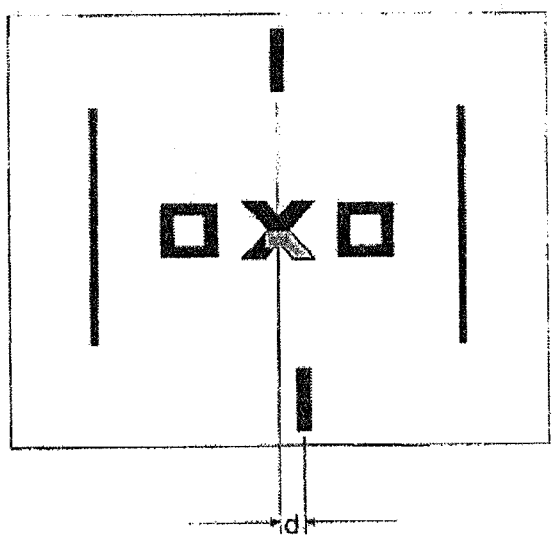
FIG. 9 shows a test figure showing the situation where the fixation disparity amount is being calculated.

Herein, in the aforementioned description, both the degree of fixation disparity represented by an angle and that represented by a distance on the screen were referred to as a "fixation disparity amount". However, in the following description, as a matter of explanatory convenience, the degree of fixation disparity that has been converted to an angle (minute) will be referred to as a "fixation disparity amount". On the other hand, as shown in FIG. 9 described later, the distance a visual target shifts on the display means 5a is simply referred to as a "shift amount".

Furthermore, the prism diopter which is a unit of prism amount indicates the degree of refraction of light. After light has passed through a prism and the light progresses one meter along the direction of the same light axis as before the passage through the prism, if the light has deviated one centimeter in the vertical direction to the direction of the same light axis as before the passage through the prism, the prism amount corresponds to one prism diopter. By use of this relationship, the "fixation disparity amount (minute)" or the "shift amount" can simply be converted to prism diopter. The details will be described later, but obviously, "to transform a fixation disparity amount (minute) into an aligning prism", which is one of major characteristics of this embodiment, is completely different from the aforementioned simple conversion. In this specification, the "conversion" to simply change a fixation disparity amount (minute) or a shift amount to prism diopter and the "transformation" to calculate an aligning prism (unit: prism diopter) from a fixation disparity amount (unit: minute) are selectively used.

5-A) Order-Placing Computer 2

The order-placing computer 2 is a computer installed on the side which asks for the acquisition of a prism prescription value (aligning prism) necessary for making a spectacle lens. To provide a specific example, it is a computer installed in an eyeglass shop. A person (who will eventually become a subject) who is thinking of buying a spectacle lens comes to an eyeglass shop. Then, by using the measuring part 5, information (i.e., fixation disparity amount) necessary for ordering a spectacle lens is acquired from the subject. After that, by using the transmission part 6, the fixation disparity amount is transmitted to the calculation part 7 of the order-receiving computer 3.

In the prism prescription value acquisition system 1 having the above configuration, the correspondence relationship between the order-placing computer 2 and the order-receiving computer 3 may be any one of the followings: 1:1 correspondence relationship, m:1 correspondence relationship ("m" is a natural number equal to or larger than 2), 1:n correspondence relationship ("n" is a natural number equal to or larger than 2), and m:n correspondence relationship. Furthermore, the order-placing computer 2 and the order-receiving computer 3 may be located in the same country or may be in different countries. Furthermore, although not shown, a configuration may be so designed that a variety of servers (e.g., data server) are connected to the communication line 4, and data may be sent and received among the servers and the order-placing computer 2 or the order-receiving computer 3 as necessary.

Herein, the order-placing computer 2 functions as a computer. A plurality of order-placing computers 2 may be located in a system.

Furthermore, the order-placing computer 2 is equipped with a control part to manage and control a variety of information used to acquire an aligning prism as well as managing and controlling each portion of the order-receiving computer 3. However, specific configuration of the control part can be embodied by use of known technology; therefore, detailed description thereof is omitted herein.

5-A-a) Measuring Part 5

Components included in the measuring part 5 of the order-placing computer 2 are as follows:

(1) A display means 5a (e.g., screen) designed to display at least one test figure, the at least one test figure including components having various different optical properties exhibited when they are displayed.

(2) An accessory device (e.g., 3D spectacles 5b, or polarized spectacles) designed based on the optical properties so that at least one first component (e.g., visual target for the right eye) is presented only to a subject's first eye (e.g., right eye) and at least one second component (e.g., visual target for the left eye) is presented only to a subject's second eye (e.g., left eye).

Herein, the test figure in this embodiment includes a first component (visual target for the right eye presented only to the right eye), a second component (visual target for the left eye presented only to the left eye), and a third component (e.g., visual target for binocular visual fixation for which a subject conducts visual fixation).

(3) A selection means 5c designed in such a way that a subject enters a selection signal, and the selection signal functions to select a parameter value that satisfies predetermined criteria when a component is displayed on the screen.

(4) An input means 5*d* designed to change, based on the control signal, the parameter for displaying a first component and/or a second component of at least one test figure so as to particularly change the location. To be specific, it is an input means 5*d* designed to generate a control signal and operable by a subject.

5-A-a1) Display Means 5*a*

5-A-a2) Accessory Device (3D Spectacles 5*b*)

The display means 5*a* has a function for displaying a visual target for the right eye presented only to the right eye, a visual target for the left eye presented only to the left eye, and a visual target for binocular visual fixation for which a subject conducts visual fixation.

To be further specific, a preferred example of the display means 5*a* is a screen capable of displaying 3D images. The visual target for the right eye is presented to the subject's right eye via 3D spectacles 5*b*, and the visual target for the left eye is presented to the subject's right eye via 3D spectacles 5*b*. Obviously, the visual target for binocular visual fixation can be presented to both eyes in common.

To provide a specific example of 3D spectacles 5*b* including 3D images, 3D images include a visual target for the left eye and a visual target for the right eye, and those images are alternately displayed on the display means 5*a* at a constant period.

On the other hand, the 3D spectacles 5*b* of this embodiment have a function as an active shutter. That is, in the 3D spectacles 5*b*, the shutter alternately opens and closes at a constant period so as to create a situation where only the left eye can see ahead and a situation where only the right eye can see ahead.

Then, the period of 3D images and the period of 3D spectacles 5*b* are synchronized with each other so that the displaying of the 3D image visual target for the right eye is synchronized with the timing at which the shutter of the 3D spectacles 5*b* intended for the right eye opens. By doing so, it is possible to display a visual target for each eye to each eye of a subject. Obviously, as well-known for stereoscopic image display apparatuses, these 3D spectacles may be based on the method that uses a polarization plate, or on other methods. For example, a display equipped with a parallax filter may be used. In this case, 3D spectacles are unnecessary. However, in this embodiment, the case where 3D spectacles are used as an accessory device will be described.

On the other hand, a visual target for binocular visual fixation is presented to both eyes in common.

In this embodiment, the display means 5*a* is so designed that at least one test figure is sequentially displayed in various different areas (e.g., right half and left half).

As stated above, the test figure in this embodiment includes a first component (visual target for the right eye presented only to the right eye), a second component (visual target for the left eye presented only to the left eye), and a third component (e.g., visual target for binocular visual fixation for which a subject conducts visual fixation).

The "visual target" in this embodiment is necessary to detect a fixation disparity amount of fixation disparity as an objective value. The visual target may be of any shape; a rod-like sign, or a character. In this embodiment, description will be made about the situation where the visual target for the left eye is provided with a vertical line at the upper center of the image, while the visual target for the right eye is provided with a vertical line (nonius line) at the lower center of the image. In this embodiment, the right eye nonius line and the left eye nonius line are used. However, the visual target for visual fixation may basically be of any shape although a shape (e.g., dot, ×, □, ○, or a combination of those) for which a subject can easily conduct visual fixation is preferred.

Furthermore, the visual target for the left eye and the visual target for the right eye each may be marked with a scale so that a subject can also recognize amount of disparity of nonius line due to a fixation disparity. In this case, the scale may be used instead of a visual target for binocular visual fixation, or the scale may be provided separately from the visual target for binocular visual fixation.

FIG. 5(*a*) shows a test figure for detecting vertical fixation disparity, and FIG. 5(*b*) shows a test figure for detecting horizontal fixation disparity. For example, as shown in FIG. 5(*a*) and FIG. 5(*b*), it is possible to use a test figure for determining an aligning prism for correcting fixation disparity. Shapes and dimensions of those test figures 50 and 55 have recently been developed by the inventor of the present invention. Those figures look alike those of the Mallett test, and the fusion target 53 (simultaneously visible to both eyes) located around the center is used as a form of a character of "OXO". One nonius line is displayed only to the right eye and the other nonius line is displayed only to the left eye. However, the points (improved points) different from the Mallett test are that, as shown in FIG. 5(*a*) and FIG. 5(*b*), the nonius lines are each distant from the center (i.e., "OXO"). This is based on the important scientific findings regarding the difference between subjective fixation disparity and objective fixation disparity. It has been proven that the test portion located at the periphery significantly matches the objective fixation disparity amount.

The size of the outer circumference of the fusion target "OXO" 53, shown at the center, corresponds to the visual angle of 13.7 minutes in the vertical and horizontal directions in one embodiment, and the height of the entire test area corresponds to the visual angle of 2.76°.

Moreover, it is preferred that a visual target for the right eye displayed on the display means 5*a*, a visual target for the left eye presented only to the left eye, and a visual target for binocular visual fixation for which a subject conducts visual fixation be included in one test figure. Then, it is preferred that the test figure be placed at the front of the background image provided with a plurality of visual targets for binocular visual fixation. By doing so, a large number of visual targets for binocular visual fixation are present on the display means 5*a*, and with regard to two visual targets, which are a visual target for the left eye and a visual target for the right eye, to be moved as described later, a large number of visual targets become the visual targets for binocular visual fixation; therefore, it is possible for a subject to more accurately conduct binocular visual fixation. As a result, it is possible to accurately measure the fixation disparity amount.

Furthermore, it is preferred that the test figure can be flexibly placed at any location at the front of the background image provided with a plurality of visual targets for binocular visual fixation. When the fixation disparity amount is measured a plurality of times, it is preferred that the location of the test figure be changed at the front of the background image every time a measurement is conducted. To provide a specific example, when measurement is conducted twice, the test figure is dynamically and alternately displayed on the right half side or the left half side of the display means 5*a* (e.g., monitor) after individual judgment has been made.

When measurement is conducted a plurality of times, if measurement is conducted at the same location on the display means 5*a*, a subject results in recognizing the test figure as an afterimage, which could possibly affect measurement accuracy. Accordingly, by adopting a configuration in which the test figure can be flexibly placed at any location at the front of the background image provided with a plurality of visual targets for binocular visual fixation, it is possible to change the location of the test figure on the background image every time a measurement is conducted. By doing so, the problem of the aforementioned afterimage can be solved, and since the visual line moves every time measurement is conducted, the subject blinks more often, thereby making it possible to reduce dryness of the eye and fatigue of the eye during measurement. Furthermore, the visual condition will be achieved that enables the stable perception of a test figure which is close to a natural visual condition and has no suppression (i.e., phenomenon that perception becomes dim or eliminated).

Furthermore, a plurality of aforementioned display means 5*a* may be installed. To provide an example, a plurality of display means 5*a* may be connected to one order-placing computer 2. One display means 5*a* is used to measure the fixation disparity amount of near vision, and another display means 5*a* is used to measure the fixation disparity amount of far vision. Obviously, a display means 5*a* may further be provided to obtain the fixation disparity amount of intermediate vision.

A display means 5*a* for near vision (for short distance display) is preferably designed to display at least one test figure at a short distance of 20 cm to 100 cm. And separately, a display means 5*a*' for far vision is provided. The display means 5*a*' for far vision (for long distance display) is preferably designed to display at least one test figure at a long distance of 3 m to 6 m (4 m to 8 m according to circumstances). Furthermore, for an examiner to control the display means 5*a*' for far vision, a second order-placing computer 2' may be installed separately from the first order-placing computer 2 equipped with a display means 5*a* for near vision.

In this embodiment, description will be made about the case where three electronic apparatuses are provided, which are a first order-placing computer 2 for near vision, a second order-placing computer 2' for far vision, and a display means 5*a*' for far vision. In this case, the first order-placing computer 2 for near vision is, for example, a tablet PC which may also function as a display means 5*a* for near vision. In this Specification, both the display means 5*a*' for far vision and the display means 5*a* for near vision are also referred to as a "display means 5*a*".

5-A-a3) Selection Means 5*c*

First, by means of a selection means 5*c*, a predetermined component (e.g., visual target for the right eye) is selected and made movable. Then, by means of the selection means 5*c*, a selection signal is entered to select a unit of movement, thereby selecting a parameter value. To provide a specific example, setting is made so that the visual target for the right eye can be moved by an angle of about 0.5 minute every time the left cursor of the keyboard is pressed. Furthermore, the distance between a subject and the display means 5*a* is selected and set by the selection means 5*c*, and fixation disparity may be measured according to the set distance.

5-A-a4) Input Means 5*d*

The input means 5*d* in this embodiment has a function for generating a control signal and moving a visual target for the left eye and/or a visual target for the right eye displayed on the display means 5*a*. Obviously, when moving the visual target for the left eye and/or the visual target for the right eye, the visual target for visual fixation is not moved.

However, when the visual target for the left eye and/or the visual target for the right eye are not moved, the visual target for visual fixation may be moved. Furthermore, by means of the operating portion, it is possible to adopt a configuration in which the test figure including a visual target for the left eye, a visual target for the right eye, and a visual target for visual fixation can be flexibly placed at a predetermined location at the front of the background image.

The input means 5*d* in this embodiment may be any component as far as it has a configuration that can move a visual target on the display means 5*a*. A known component may be used. Examples of known components include a keyboard connected to the display means 5*a*, mouse, game controller (game pad) used for playing games, joystick, and contact sensing film (touch panel) of the screen.

When a subject itself moves a visual target, it is possible for the subject to find the state in which visual targets are perceived as being aligned. Accordingly, it is possible to create a state in which visual targets are perceived as being aligned as the result of reflecting the perception of the subject. On the other hand, on the display means 5*a*, it is possible to accurately acquire a fixation disparity amount. Furthermore, interactive operations are possible that allow a subject itself to move a visual target. Also, it is possible to accurately acquire a fixation disparity amount by very simple operations, such as pressing a key of the keyboard, or manipulating the controller for a game; thus it is possible to provide a user-friendly system.

As stated above, it is significantly advantageous to provide an input means 5*d* having a configuration that enables a subject itself to flexibly move each visual target displayed on the display means 5*a*. Definitely, the aforementioned contents do not prevent a person other than a subject (e.g., examiner) from operating the input means 5*d*.

5-A-a5) Other Devices

Figure 4:
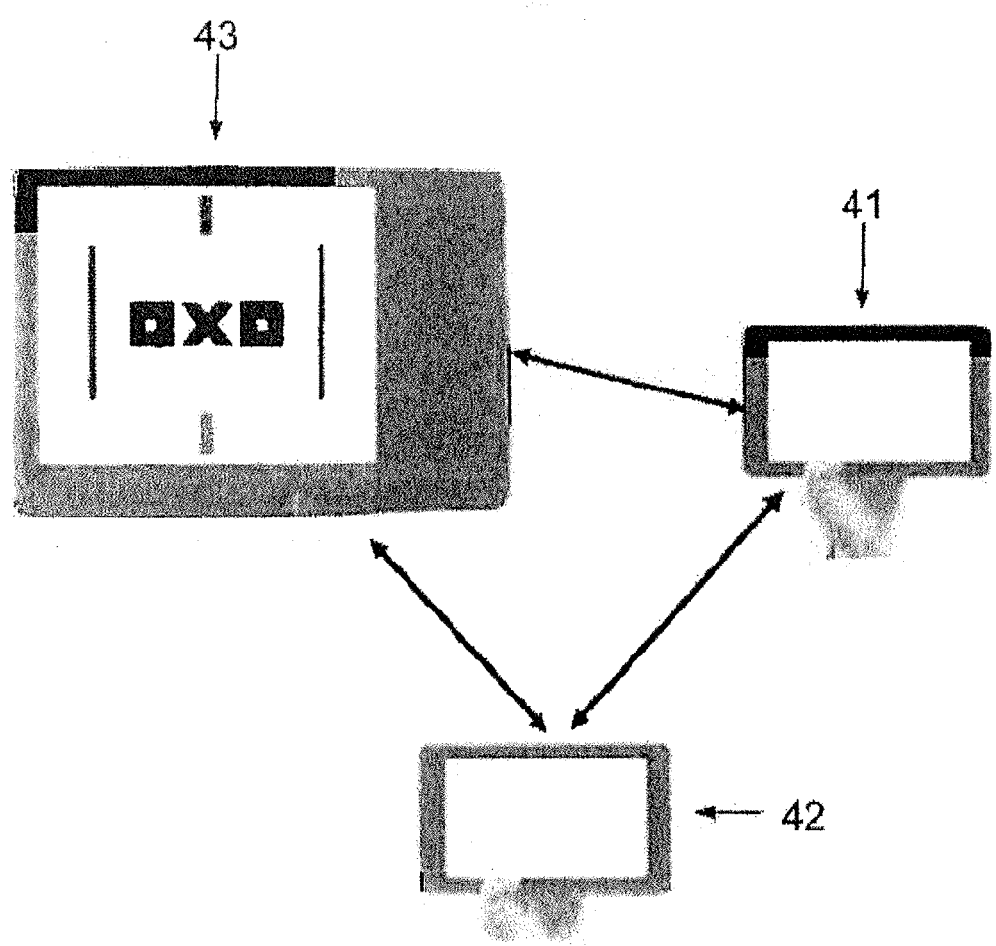
FIG. 4 is a schematic diagram showing a configuration of an apparatus for measuring fixation disparity.

It is preferred if the following components or functions are provided for an order-placing computer 2. Explanation will be given with reference to FIG. 4 which is a schematic diagram showing the configuration of an apparatus for measuring fixation disparity. Although some contents overlap with the components stated above, description will be given again.

A wireless network connection for controlling far distance and near distance display A touch screen provided with a simple menu A voice navigation (e.g., one-way wireless headphones) for instructing an operator about the next examination step A base station for fixing a tablet PC. By means of this, an examiner can use both hands to adjust the trial frame and replace trial lenses. This will be described later as another embodiment.

A commercially-available tablet PC equipped with a 7- to 12-inch display, or a laptop with a maximum display size of 15 inches, or appropriate similar electronic apparatus.

The computer for far distance display is a commercially-available computer equipped with a monitor (or PC-incorporated monitor) for displaying 2D and 3D images when showing test figures for far vision (4 to 8 meters, preferably, 4.5 to 6 meters) and is used for displaying static and dynamic test figures as 2D and 3D images. The screen 43 is controlled by an apparatus 42 for examiner for the sake of the examiner and connected to an apparatus 41 for subject to display results of the operation conducted by a subject.

Herein, the apparatus 41 for subject is an order-placing computer, also functioning as a computer for subject, equipped with at least an input means and a transmission part of the measuring part. Furthermore, the apparatus 42 for examiner is an order-placing computer, also functioning as a computer for examiner, equipped with a selection means and a transmission part of the measuring part. The screen 43 corresponds to a display means 5*a*.

Furthermore, preferred components or functions provided for the display means 5*a* (screen 43) of the computer for far distance display are as follows:

- An electronic apparatus for displaying visual targets, equipped with at least one 22- to 28-inch 16×9 TFT/LCD/LED monitor and generally used for optometry.
- Resolution of at least 1980×1080 pixels.
- Visible surface of the display of at least 50×29 cm.
- Brightness of at least 220 cd/m$^2$.
- 3D display by, for example, polarization or shutter technology.
- Operation by a built-in microprocessor, the apparatus 42 for examiner enables wireless control by the examiner, the apparatus 42 for examiner is interactively connected with the apparatus 41 for subject for near distance display.
- Observation distance of from 4 to 8 meters.

On the other hand, the computer for near distance display is a commercially-available 3D-performance tablet PC for displaying 2D and 3D images when showing test figures for near vision and is used for a subject to interactively utilize the PC in both measurement methods for far distance and near distance display. For example, the subject adjust the position of nonius lines of test figures which displayed on the far distance display or the near distance display by use of the tablet PC for the near distance display. The apparatus 41 for subject is an interactive fixation disparity measurement apparatus for near distance to display static and dynamic test figures as 2D and 3D images and also functions as an operation apparatus for subject that uses, for example, a touch screen.

Preferred components or functions provided for the display means 5*a* (screen 43) of the computer for near distance display are as follows:

- A commercially-available tablet PC equipped with a 7- to 12-inch 3D performance display.
- 3D display by, for example, dynamically corrected cylindrical grids, shutter technology, color codes or polarization.
- Connected to a computer, which is controlled by an apparatus 42 for examiner via wireless network connection and equipped with a screen 43 for interactively judging the test figures.
- A parameter of a test figure, specifically the location of a nonius line, is changed by a simple menu control with a few button operations, and judgment is made as a signal to select "right or left" or "up or down" and "centering (the state in which nonius lines are being aligned)" with respect to a test figure.
- Operation by a subject is also possible by means of the surface of the contact sensitive touch panel. A subject moves a sensor to an appropriate direction by using an accelerating sensor of the apparatus, thereby showing the subject's own perception to the outside.
- It is also possible to conduct the aforementioned operations by means of voice control or gesture.

5-A-b) Transmission Part 6

The fixation disparity amount obtained by the aforementioned measuring part 5 is transmitted to the calculation part 7 of the order-receiving computer 3 by the transmission part 6. For transmission, as stated above, a public line may be used or a dedicated line may be used. In this embodiment, description has been given about an example where a calculation part 7 is provided in the order-receiving computer 3; however, obviously, the order-placing computer 2 may be equipped with the calculation part 7. In such a configuration, the fixation disparity amount obtained by the measuring part 5 is also transmitted to the calculation part 7 by the transmission part 6.

Those mentioned above are the portions related to the order-placing computer 2. Hereinafter, the order-receiving computer 3 connected to the order-placing computer 2 via a communication line 4 will be described.

5-B) Order-Receiving Computer 3

An order-receiving computer 3 is a computer installed on the side where an aligning prism necessary for producing a spectacle lens is acquired. To provide a specific example, it is a computer installed in a spectacle lens manufacturing factory. When an order for production of a spectacle lens placed by an eyeglass shop is received, the calculation part 7 of the order-receiving computer 3 calculates and acquires, based on the fixation disparity amount, an aligning prism necessary for a spectacle lens worn by a subject.

The order-receiving computer 3 has a function as a computer. A plurality of order-receiving computers 3 may be provided in a system.

Furthermore, the order-receiving computer 3 is equipped with a control part for managing and controlling a variety of information used to acquire an aligning prism, managing and controlling each portion of the order-receiving computer 3, and calculating and acquiring an aligning prism. However, the specific configuration of the control part may be embodied by use of known technology, and detailed description thereof will be omitted herein.

5-B-a) Calculation Part 7

The calculation part 7 in this embodiment has a function to transform the fixation disparity amount calculated by the measuring part 5 and transmitted by the transmission part 6 into an aligning prism. As described in non-patent document 1, although the relationship between the "fixation disparity" and the "aligning prism" depends on differences among individuals, by means of the aforementioned transformation, it is possible to calculate an aligning prism capable of eliminating fixation disparity of each subject.

The aligning prism is calculated according to the following equation:

$$AP_{ver}=k_{ver}*FD_{ver}$$

$$AP_{hor}=k_{hor}*FD_{hor} \quad \text{(Equation 1)}$$

$AP_{ver}$ represents a prism amount (unit: prism diopter) in the vertical direction (top and bottom direction) in the aligning prism, $AP_{hor}$ represents a horizontal direction prism amount in the aligning prism, and $FD_{ver}$ represents a fixation disparity amount in the vertical direction.

$FD_{hor}$ represents a fixation disparity amount in the horizontal direction; however, each of coefficients $k_{hor}$ and $k_{ver}$ satisfies the following conditions:

$$0.3 \leq k_{ver} \leq 0.7$$

$$1.4 \leq k_{hor} \leq 2.0$$

Incidentally, as $FD_{ver}$ and $FD_{hor}$, for example, the result obtained by near distance display may be set as $FD_{ver}$ and $FD_{hor}$, or reversely, the result obtained by far distance display may be set as $FD_{ver}$ and $FD_{hor}$. However, $FD_{ver}$ and $FD_{hor}$, are preferably calculated using the following technique.

An outline of this technique is as follows.

1. In order to confirm reliability of measurement itself of the fixation disparity (possibility that an examinee has a visual problem depending on a case), the measurement is performed twice under the same condition, and whether or not a standard deviation between the fixation disparity amounts in each measurement is within a defined value, is confirmed.

2. If the deviation is excessively large between the fixation disparity amount obtained by far distance, and the fixation disparity amount obtained by near distance, there is a possibility that the examinee has a visual problem, and an accurate fixation disparity amount cannot be measured. Therefore, whether or not a difference between the fixation disparity amount obtained by far distance and the fixation disparity amount obtained by near distance, is within a defined value, is confirmed.

First, the procedure of the abovementioned 1 will be described. First, in order to confirm the reliability of the measurement itself of the fixation disparity, the measurement is performed twice under the same condition. At this time, as described in 5-A-a 1) displayer 5a, when a plurality of measurements are performed, a location of visual target on the display is preferably changed in each measurement, in a front surface of a background image on the display.

A measurement method of the specific individual fixation disparity amount, is described in <8. Acquisition method of prism prescription value>

Here, for example, the fixation disparity amount obtained by a first measurement out of a plurality of measurements, is called FDFh1, and the fixation disparity amount obtained by a second measurement out of a plurality of measurements is called FDFh2, which is the measurement of the fixation disparity amount in a horizontal direction performed in far distance.

Similarly, the fixation disparity amount obtained by the first measurement out of a plurality of measurements is called FDFv1, and the fixation disparity amount obtained by the second measurement out of a plurality of measurements is called FDFv2, which is the measurement of the fixation disparity amount in a vertical direction performed in far distance.

Also, the fixation disparity amount obtained by the first measurement out of a plurality of measurements is called FDNh1, and the fixation disparity amount obtained by the second measurement out of a plurality of measurements is called FDNh2, which is the measurement of the fixation disparity amount in a horizontal direction performed in near distance.

Similarly, the fixation disparity amount obtained by the first measurement out of a plurality of measurements is called FDNv1, and the fixation disparity amount obtained by the second measurement out of a plurality of measurements is called FDNv2, which is the measurement of the fixation disparity amount in a vertical direction performed in far distance.

Before the abovementioned procedure of 1, whether or not each fixation disparity amount is excessively large, is judged. This is because if each fixation disparity amount is excessively large, there is a possibility that the examinee has a visual problem such as a strabismus, and in this case, the aligning prism cannot be appropriately obtained. For example, when each fixation disparity amount exceeds 5 minutes of arc, this value is excluded or the measurement itself is stopped.

Through the abovementioned preparation, first, the measurement of the fixation disparity amount in the horizontal direction in far distance, is performed twice. Then, the standard deviation between the fixation disparity amounts in each measurement is obtained by the following equation.

$$\text{Standard deviation (SD) (Unit: minute)} = \text{SQRT}[\{(FDFh1-M)^2 + (FDFh2-M)^2\}/2] \quad \text{(Equation 2)}$$

Wherein M=(FDFh1+FDFh2)/2

When SD is 1.25 minutes or less, it is judged that the reliability of the measurement itself of the fixation disparity amount can be secured. Then, an average value FDFha of two measurements, is stored as the "value of the fixation disparity amount in the horizontal direction in far distance". This work corresponds to the first and second measurements in the <8. Acquisition method of prism prescription value>.

When SD exceeds 1.25 minutes, a similar measurement is performed again in view of the possibility that a measurement error occurs. Namely, third and fourth measurements are performed, and the fixation disparity amount (FDFh3 and FDFh4) in each measurement is obtained. Then, SD is calculated again.

In this case as well, when SD exceeds 1.25 minutes again, the reliability of the measurement itself of the fixation disparity cannot be secured, and therefore the measurement is stopped. Further, in view of the possibility that the examinee has a visual problem, the display means 5a displays a message showing accordingly to the examinee.

On the other hand, when SD is 1.25 minutes or less, the average value FDFha of the fixation disparity amount FDFh3 in the third measurement and the fixation disparity amount FDFh4 in the fourth measurement, is stored as the "value of the fixation disparity amount in the horizontal direction in far distance" in "the first work described in the <8. Acquisition method of the prism prescription value> described later).

The procedure of the abovementioned measurement is performed in the vertical direction in far distance, in the horizontal direction in near distance, and in the vertical direction in near distance. A reference value of SD in the horizontal direction is set to 1.25 minutes, and a reference value of SD in the vertical direction is set to 0.5 minutes.

The procedure of the abovementioned 2, will be described next. That is, if the deviation is excessively large between the fixation disparity amount in far distance and the fixation disparity amount in near distance, it is confirmed whether or not there is a possibility that the examinee has a visual problem.

By the procedure of the abovementioned 1, the value (FDFha) of the fixation disparity amount in the horizontal direction in far distance and the value (FDNha) of the fixation disparity amount in the horizontal direction in near distance, the value (FDFva) of the fixation disparity amount in the vertical direction in far distance, and the value (FDNva) of the fixation disparity amount in the vertical direction in near distance, can be obtained.

Before the procedure of 2, it is confirmed whether or not each fixation disparity amount is not an excessively large value. This is because if each fixation disparity amount is the excessively large value, an accurate aligning prism cannot be obtained. that is, if any one of FDFha, FDNha, FDFva, and FDNva exceeds 5 minutes, the display means 5a displays a message showing accordingly to the examinee.

Then, the procedure of 2 is performed.

This time, difference (ΔFDha) is obtained between the value (FDFha) of the fixation disparity amount in the horizontal direction in far distance and the value (FDNha) of the fixation disparity amount in the horizontal direction in near distance, and a final value $FD_{hor}$ of the fixation disparity amount in the horizontal direction, is obtained as follows.

When the values of FDFha and FDNha are respectively close to zero, a finally obtained $FD_{hor}$ may be considered to be zero. Specifically, there is a case that an absolute value of FDFha is less than 0.15, and an absolute value of FDNha is 0.15 minutes or less.

When ΔFDha is 1.25 or less, a finally obtained $FD_{hor}$ is determined in accordance with the following content.

[The Case when Signs of (+−) is the Same Between FDFha and FDNha]

First, a larger absolute value of FDFha and FDNha is defined as $FD_{max}$, and a smaller absolute value of FDFha and FDNha is defined as $FD_{min}$, and $FD_{hor}$ is determined by the following equation, wherein weighing is carried out.

$$FD_{hor}=(FD_{max}*0.6)+(FD_{min}*0.4) \quad \text{(Equation 3)}$$

In the horizontal direction, a plus sign of the fixation disparity amount shows an exo fixation disparity amount, and a minus sign of the fixation disparity amount shows an eso fixation disparity amount.

Also, in the vertical direction, a plus sign of the fixation disparity amount shows a downward fixation disparity amount in the left eye and an upward fixation disparity amount in the right eye, and a minus sing of the fixation disparity amount shows an upward fixation disparity amount in the left eye and a downward fixation disparity amount in the right eye.

[The Case that Sign (+−) is Different Between FDFha and FDNha]

$FD_{hor}$ is determined by the following equation.

$$FD_{hor}=(FDFha*0.5)+(FDNha*0.5) \quad \text{(Equation 4)}$$

When ΔFDha exceeds 1.25 minutes and is 2.5 minutes or less, a finally obtained $FD_{hor}$ is determined in accordance with the following content.

[The Case when Sign (+−) is the Same Between FDFha and FDNha]

First, a larger absolute value of FDFha and FDNha is defined as $FD_{max}$, and a smaller absolute value of FDFha and FDNha is defined as $FD_{min}$, and $FD_{hor}$ is determined by the following equation, wherein weighing is carried out.

$$FD_{hor}=(FD_{max}*0.6)+(FD_{min}*0.4) \quad \text{(Equation 5)}$$

[The Case when Sign (+−) is Different Between FDFha and FDNha, and when FDFha is Less than 0.3 Minutes and Sign of FDNha is +]

$FD_{hor}$ is determined by the following equation.

$$FD_{hor}=FDNha*0.5 \quad \text{(Equation 6)}$$

At this time, there is a possibility that an addition power is excessively strong, and therefore the display means 5a displays accordingly.

[The Case when Sign (+−) is Different Between FDFha and FDNha, and when FDFha is Less than 0.3, and Signs of FDNha is −]

$FD_{hor}$ is determined by (Equation 6)

At this time, there is a possibility that the addition power is excessively weak, and therefore the display means 5a displays accordingly.

[The Case when Sign (+−) is Different Between FDFha and FDNha, Corresponding to None of the Above Cases]

$FD_{hor}$ is determined by (Equation 6).

When ΔFDha exceeds 2.5 minutes, the measurement is stopped, and in view of the possibility that the examinee has a visual problem, the display means 5a displays the message showing accordingly to the examinee.

Next, difference (ΔFDva) between the value (FDFva) of the fixation disparity amount in the vertical direction in far distance, and the value (FDNva) of the fixation disparity amount in the vertical direction in near distance, is obtained, and a final horizontal fixation disparity amount value $FD_{ver}$ is obtained as follows.

When the values of FDFva and FDNva are respectively close to zero, a finally obtained $FD_{ver}$ may be considered to be zero. Specifically, there is a case that an absolute value of FDFva is less than 0.2, and an absolute value of FDNva is 0.2 minutes or less.

When ΔFDva is 2.0 minutes or less, a finally obtained FDver is determined in accordance with the following equation 7.

$$FDver=(FDFva*0.5)+(FDNva*0.5) \quad \text{(Equation 7)}$$

When ΔFDva exceeds 2.0 minutes, the measurement is stopped, and in view of the possibility that the examinee has a visual problem, the display means 5a displays the message showing accordingly to the examinee.

As described above, $FD_{hor}$ and $FD_{ver}$ are preferably obtained.

The above standard deviation, difference of the value of the fixation disparity amount between far distance and near distance, judgment of the value of the fixation disparity amount, and further judgment of the value of the aligning prism described later, may be performed by a judgment part 8 described later.

The above (equation 1) (specifically, coefficient $k_{ver}$ and $k_{hor}$) was found as the result of the inventor's unparalleled efforts. The relationship between the fixation disparity amount and the aligning prism obtained by this measurement is shown in FIG. 12(a) and FIG. 12(b).

Figure 12:
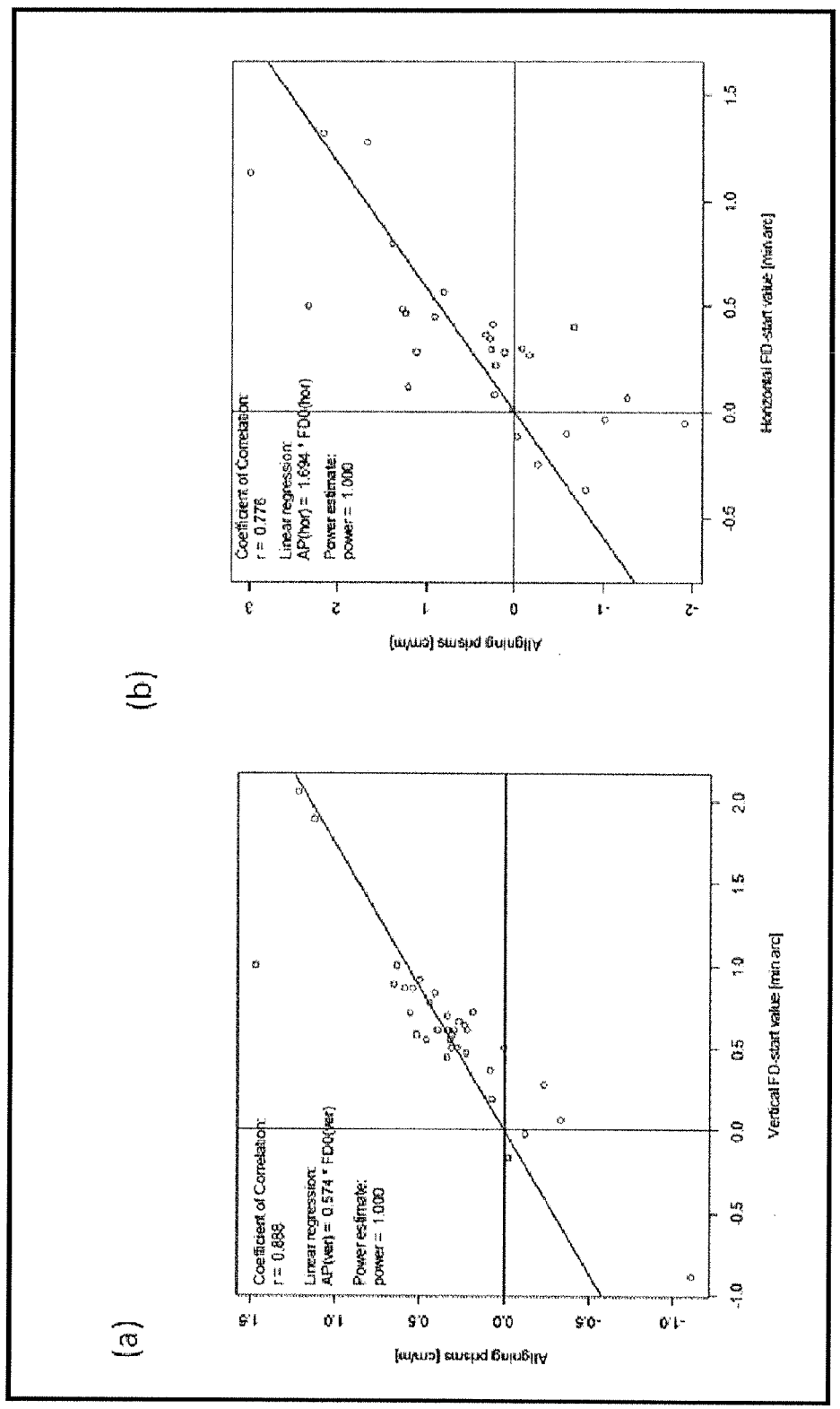
FIG. 12(a) shows the relationship between the fixation disparity amount in the horizontal direction (horizontal axis) and the aligning prism (vertical axis).
FIG. 12(b) shows the relationship between the fixation disparity amount in the vertical direction (horizontal axis) and the aligning prism (vertical axis).

FIG. 12(a) shows the relationship between the vertical direction fixation disparity amount (horizontal axis; unit: minute) and the vertical direction aligning prism (vertical axis; unit: prism diopter). When the sign is positive, lower fixation disparity of the left eye and upper fixation disparity of the right eye are indicated; and when the sign is negative, upper fixation disparity of the left eye and lower fixation disparity of the right eye are indicated.

FIG. 12(b) shows the relationship between the horizontal direction fixation disparity amount (horizontal axis; unit: minute) and the horizontal direction aligning prism (vertical axis; unit: prism diopter). When the sign is positive, exo fixation disparity is indicated; and when the sign is negative, eso fixation disparity is indicated.

In each figure, the number of subjects is 34, and the fixation disparity amount and the aligning prism are measured for each subject.

Furthermore, as stated above, measurement of the fixation disparity amount is conducted by use of a visual target for the right eye, a visual target for the left eye, and a visual target for binocular visual fixation. The measurement of the aligning prism is conducted by use of a trial lens, and a prism amount of the trial lens that has eliminated fixation disparity is adopted.

The rectilinear graph shown in FIG. 12(a) is a regression line indicating the relationship between the fixation disparity amount and the aligning prism in the vertical direction that was obtained by statistical analysis based on the relationship between the vertical direction fixation disparity amount and the vertical direction aligning prism. The regression line was obtained by use of robust regression of statistical analysis. The correlation coefficient of the regression line indicating the relationship between the fixation disparity amount and the aligning prism in the vertical direction is 0.888.

The rectilinear graph shown in FIG. 12(b) is a regression line indicating the relationship between the fixation disparity amount and the aligning prism in the horizontal direction that was obtained by statistical analysis based on the relationship between the horizontal direction fixation disparity amount and the horizontal direction aligning prism. The regression line was obtained by use of robust regression of statistical analysis. The correlation coefficient of the regression line indicating the relationship between the fixation disparity amount and the aligning prism in the horizontal direction is 0.776.

Furthermore, verification capability of the statistical analysis has reached 1.000 when those regression lines indicating the relationship between the fixation disparity amount and the aligning prism in the vertical direction and in the horizontal direction were obtained.

Based on those regression lines, it became possible to obtain aligning prisms from the vertical and horizontal direction fixation disparity amounts according to the relational expression described below. An equation in which the value of the gradient of the regression line is applied to the above calculation formula is as follows:

$$AP_{ver}=0.574*FD_{ver}$$

$$AP_{hor}=1.694*FD_{hor} \quad \text{(Equation 8)}$$

Herein, both $FD_{ver}$ and $FD_{hor}$ are fixation disparity amounts which were measured without mounting a trial lens provided with a prism to a trial frame. A trial frame equipped with a trial lens provided with a prism is referred to as "measurement spectacles".

At this time, it is preferably judged whether each aligning prism is excessively large. If each aligning prism is excessively large, there is a possibility that the examinee has a visual problem such as a strabismus, and there is a possibility that the examinee has a problem other than solving the fixation disparity. For example, when each aligning prism exceeds 5.0Δ, the measurement itself is stopped.

Obviously, (equation 8) in which the value of the gradient of the regression line is applied to (equation 1) is a significantly preferred example. Even if a value other than the above value but close to it is set for a coefficient, it is possible to calculate an aligning prism from the fixation disparity amount measured without mounting a prism lens to a trial frame and the direction.

Furthermore, the data of a small amount of fixation disparity, data of less than 0.5, which is considered relatively unreliable and erroneous as to measurement is excluded from all of the samples, and when the range of the coefficient of $k_{ver}$ is estimated based on the remaining data, it is found that the coefficient concentrates in the range of $0.3 \leq k_{ver} \leq 0.7$. Therefore, in the range of $0.3 \leq k_{ver} \leq 0.7$, accurately transforming the fixation disparity amount into an aligning prism becomes more reliable.

The same thing can also be found based on FIG. 12(b). The data of a small amount of fixation disparity, data of less than 0.5, which is considered relatively unreliable and erroneous as to measurement is excluded from all of the samples, and when the range of the coefficient of $k_{ver}$ is estimated based on the remaining data, it is found that accurately transforming the fixation disparity amount into an aligning prism becomes more reliable in the range of $1.4 \leq k_{hor} \leq 2.0$.

To summarize the contents, after all, as the result of obtaining the calculation formula regarding $AP_{ver}$ and $AP_{hor}$, the findings have been obtained that if the fixation disparity amount is a predetermined angle (e.g., at least within ±4 minutes as indicated by the above measurement; hereinafter, referred to as "4 minutes or less" as an absolute value), it is possible to calculate an aligning prism from the fixation disparity amount and its direction measured without using prism trial lenses.

According to this method, since prism lenses do not have to be mounted to a trial frame during the process of obtaining an aligning prism, the time for measurement is several minutes, which is significantly decreased. Furthermore, the measurement procedure becomes lot simpler because prism lenses for the trial frame do not have to be replaced and a subject does not have to wear the trial frame again and again.

Furthermore, it is preferred that the fixation disparity amount of a subject be equal to or smaller than a predetermined angle when the above calculation is conducted. If the fixation disparity amount is too large, reliability of calculation at the time of accurate transformation into an aligning prism decreases. To provide an example, the "predetermined angle" is, for example, 4 minutes or less. As stated above, FIG. 12(a) and FIG. 12(b) show the results of the above measurement conducted for a subject whose fixation disparity amount is 4 minutes or less. Obviously, the predetermined angle is not intended to be limited to 4 minutes, and if the angle is properly set to 6 minutes or less as an absolute value, it is possible to accurately transform the fixation disparity amount into an aligning prism.

Since in the above equation, the fixation disparity amount is expressed in angle, the coefficient is within the above-mentioned range. If the fixation disparity amount is expressed in distance (e.g., meter), which means that the "shift amount" is applied to the above equation, the coefficient naturally changes. However, if a unit of "shift amount (unit: meter)" is changed to a unit of the "fixation disparity amount (unit: minute)", the coefficient in the equation is within the range as mentioned above. That is, even if the shift amount (unit: meter) is used and an equation that uses a coefficient deviated from the above-mentioned range is adopted, so long as a coefficient of the equation in which the shift amount (unit: meter) has been converted to the fixation disparity amount (unit: minute) is within the above-mentioned range, the coefficient belongs to the range of the present invention even if the shift amount (unit: meter) is used.

As stated above, it is certainly possible to determine whether the subject has fixation disparity or not by detecting a fixation disparity amount of the visual targets on the display means 5a, and it is also possible to make the degree of fixation disparity into data as a fixation disparity amount and transform the fixation disparity amount into an aligning prism for a spectacle lens. As a result, it is possible to provide a spectacle lens capable of effectively correcting fixation disparity of the subject.

As an example of a technique of reflecting the above-mentioned $AP_{ver}$ and $AP_{hor}$ on the spectacle lens, a technique of distributing $AP_{ver}$ and $AP_{hor}$ to a lens for the right eye and a lens for the left eye.

For example, regarding $AP_{hor}$, a prism prescription value of the lens for the right eye and a prism prescription value for the lens for the left eye are respectively $AP_{hor}/2$. At this time, when the sign of $AP_{hor}$ is positive, a base direction of the aligning prism is outward, and meanwhile, when $AP_{hor}$ is negative, the base direction of the aligning prism is inward.

Similarly, $AP_{ver}$ is also distributed to the lens for the right eye and the lens for the left eye. At this time, when the sign of $AP_{ver}$ is positive, the base direction of the aligning prism is downward of the base in a case of the lens for the right eye, and upward of the base in a case of the lens for the left eye, and meanwhile, when the sign of $AP_{ver}$ is negative, the base direction of the aligning prism is upward of the base in the case of the lens for the right eye, and downward of the base in the case of the lens for the left eye.

In the case of using (Equation 8), an example of specific numerical values of each fixation disparity amount and each aligning prism are shown below.

The fixation disparity amount (FDFha) in the horizontal direction in far distance=−1.0 minutes The fixation disparity amount (FDNha) in the horizontal direction in near distance=−1.8 minutes The fixation disparity amount (FDFva) in the vertical direction in far distance=0.9 minutes The fixation disparity amount (FDNva) in the vertical direction in near distance=1.2 minutes $FD_{hor}$=−1.48 minutes
$AP_{hor}$=−2.51Δ
$FD_{ver}$=1.05 minutes
$AP_{ver}$=0.60Δ

Aligning prism in the lens for the right eye=1.25Δ (inward) & 0.30 (downward)

Aligning prism in the lens for the left eye=1.25Δ (inward) & 0.30 (upward)

Furthermore, it is preferred that the calculation part 7 provide an encrypted aligning prism. With the encrypted final results, only duly-authorized spectacle lens manufacturers can use the measurement results. By doing so, only spectacle lenses capable of accurately correcting fixation disparity are placed on the market.

Obviously, components other than the aforementioned portions may be provided for the prism prescription value acquisition system 1 according to this embodiment. For example, as stated above, a recording part for recording a variety of information, a server, and a communication line 4 may be separately provided.

Needless to say, the aforementioned aligning prism is not the "one obtained by converting a fixation disparity amount to a prism amount based on the distance between a visual target and a subject". To obtain a fixation disparity amount (angle), both the shift amount and the distance between the subject and the display means 5a. However, once the fixation disparity amount (angle) has been acquired, by making use of the calculation part 7 of this embodiment (making use of equations 1 or 8), the distance between the subject and the display means 5a becomes unnecessary during the process of transformation into the aligning prism. This is the point that is completely different from the simple conversion from the fixation disparity amount into the prism amount.

6. Prism Prescription Value Acquisition Apparatus

In the aforementioned embodiment, description was made about the case where the order-placing computer 2 and the order-receiving computer 3 share their roles to acquire an aligning prism. On the other hand, one of the features of the present invention is to acquire an aligning prism by transforming the fixation disparity amount into the aligning prism. Therefore, the present invention has been incorporated into the prism prescription value acquisition apparatus for acquiring an aligning prism calculated based on the fixation disparity amount, which is a significant technical feature.

The prism prescription value acquisition apparatus, described herein, is sufficient if it is equipped with at least a calculation part 7. Obviously, portions other than the calculation part 7 may be properly provided. Moreover, it is preferred that the prism prescription value acquisition apparatus be equipped with all appropriate portions. With this configuration, it is possible for eyeglass shops to acquire aligning prisms, and the eyeglass shops can transmit, to spectacle lens manufacturers, information necessary for manufacturing spectacle lenses along with prescription values other than the aligning prisms.

The preferred embodiment of the prism prescription value acquisition apparatus is as described in the preferred portions constituting a prism prescription value acquisition system 1. The preferred prism prescription value acquisition apparatus is a prism prescription value acquisition system 1 equipped with preferred portions.

7. Prism Prescription Value Acquisition Program

Furthermore, the present invention has been incorporated into a prism prescription value acquisition program that makes a computer function as a calculation part 7 for acquiring an aligning prism calculated based on the fixation disparity amount, which is a significant technical feature. Obviously, the present invention has also been incorporated into a recording medium that stores the prism prescription value acquisition program, which is a significant technical feature.

The prism prescription value acquisition program, described herein, is sufficient if it is installed in each computer and can make a computer function as at least a calculation part 7 according to instructions issued by the control part. Obviously, the program may make a computer properly function as each portion other than the calculation part 7. Furthermore, it is preferred that the program make a computer function as the calculation part 7 as well as other portions.

The preferred embodiment of the prism prescription value acquisition program is as described in the preferred portions constituting a prism prescription value acquisition system 1. The preferred prism prescription value acquisition program is a prism prescription value acquisition system 1 equipped with preferred contents.

8. Prism Prescription Value Acquisition Method

Hereinafter, specific procedures for acquiring a prism prescription value will be described. Outline of the procedures is as shown below.

First, as advance preparation for the measurement of the fixation disparity amount, a stereoscopic vision test is implemented. This is because if a subject does not have a normal stereoscopic vision, measurement of the fixation disparity amount ends up being useless.

The order-placing computer 2 is equipped with a display means 5a, 3D spectacles 5b, a selection means 5c, and an input means 5d.

Then, operating the input means 5d will measure the fixation disparity amount.

After that, the fixation disparity amount is transmitted to the calculation part 7 where it is transformed into an aligning prism. Obviously, other information (such as the prescription value as to the spectacle lens) may be transmitted at the same time.

Figure 14:
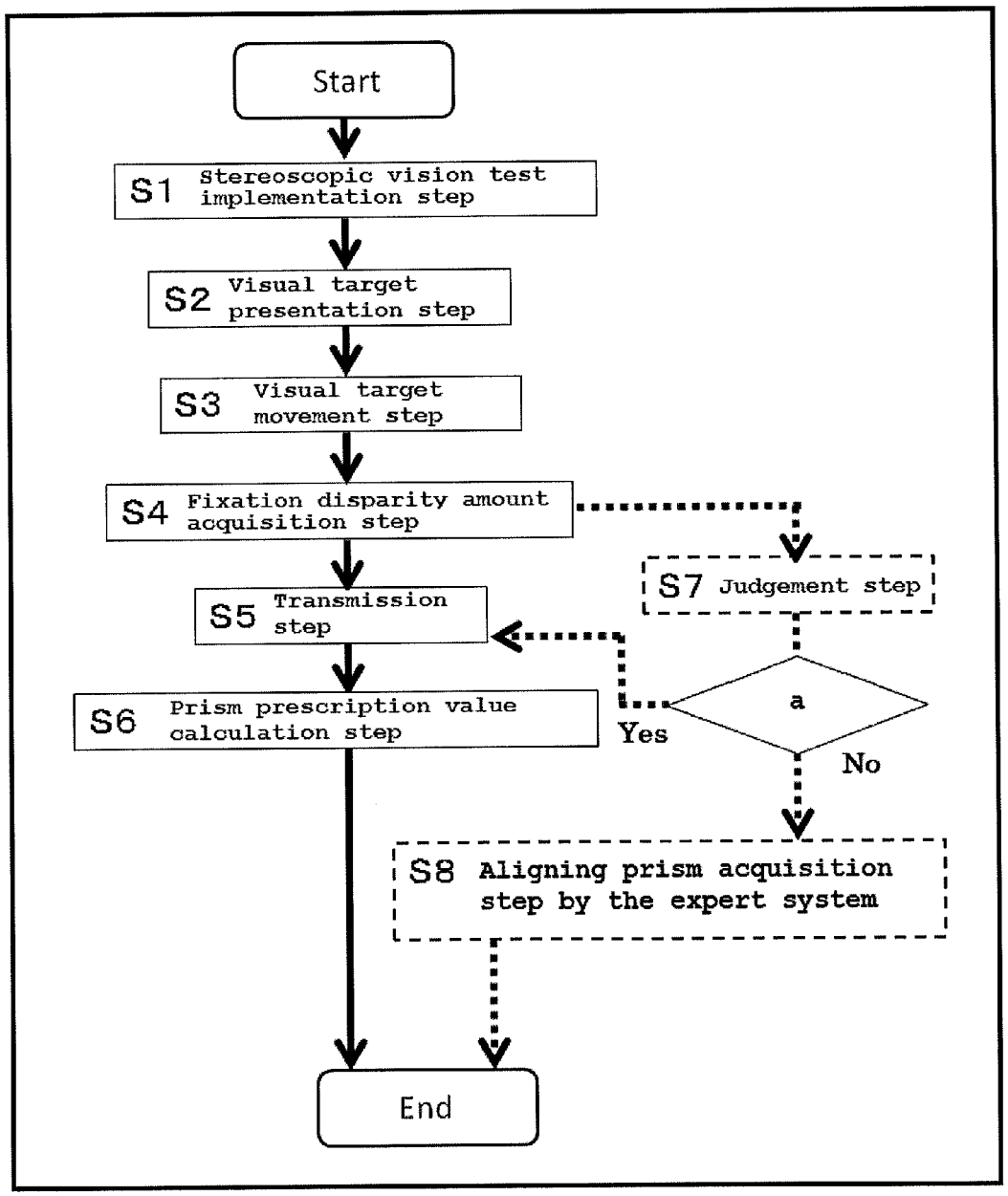
FIG. 14 is a flowchart showing the procedure for acquiring a prism prescription value in this embodiment.

Hereinafter, specific procedures for acquiring a prism prescription value will be described step by step with reference to FIG. 14. FIG. 14 is a flowchart showing the procedures for acquiring a prism prescription value in this embodiment.

(S1 Stereoscopic Vision Test Implementation Step)

As advance preparation for the measurement of the fixation disparity amount, it is reasonable to first confirm that three-dimensional vision exists as overall stereoscopic vision by implementing a stereoscopic vision test, for example, a random dot stereo test. If a person who failed this test because of lack of normal stereoscopic vision (also referred to as "micro strabismus") is found, the person can consult with an expert. In that case, a prism lens that serves as a spectacle lens will not be given to the subject. Even if the above-mentioned test figure is tilted or moved, measurement results will not be impaired. The reason is that the test figure is so formed that even if it is tilted or moved, the change is almost unrecognizable to monocular vision. By this configuration, it is possible to prevent the misjudgment that the subject has stereoscopic vision.

Another example is to apply an improved version of so-called Lang stereo test for near distance display. The aforementioned random dot test is used for quickly determining whether overall stereoscopic vision exists and determination of the prism is meaningful or whether random dot stereoscopic vision does not exist and there are risks of deteriorating the vision because of the prism. On the other hand, an advantage of the Lang test is that to provide testing at a minimum apparatus cost, for example, stereoscopic vision targets displayed on the test card are viewed without needing spectacles. On the contrary, a disadvantage of the Lang test is that when the test card is moved or tilted, hidden stereoscopic vision targets become visible. This could possibly bring a wrong result.

The basic subject herein is that even if the card is tilted or moved, a subject who has no stereoscopic vision should not recognize the stereoscopic vision target.

The initial basis for stereoscopic vision perception of the random dot pattern (random dot stereoscopic vision) was developed by B. Julesz. The difference from other stereoscopic vision tests is that the target has no configuration recognized monocularly. To achieve a stereoscopic vision, a method is required for creating different images to the right eye and to the left eye. The random dot stereo test consists of contingently disposed dot patterns, so-called matrixes. Inside the matrix, there is a geometrically-defined dot area, which is a submatrix. Although dots are disposed in various locations in the matrix, dots are uniformly disposed in the submatrix. To achieve a stereoscopic vision, submatrixes are moved on both images. Impression of the depth of the geometrically defined submatrix is not recognized until it is viewed with stereoscopic vision. As submatrixes move less, stereoscopic vision effects decrease.

Another method, the cylindrical grid technique, was invented by W. R. Hess. Patent was granted in 1912 in Germany (GB1912130347), and the technique was used for creating a so-called "similar image". The image is separated by many uniform planar cylinders disposed in parallel. There are two or more continuous images under each planar cylinder. Those continuous images are formed in various different ways by the planar cylinders. Therefore, the right eye sees different continuous images from the left eye.

Figure 11:
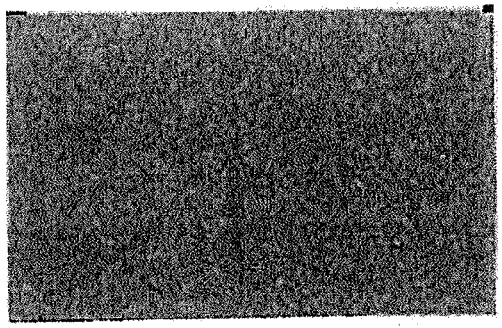
FIG. 11 shows test figures for checking the stereoscopic visual acuity.
Figure 11:
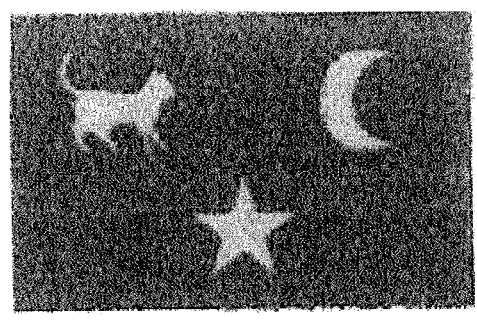

The improved version of the Lang stereoscopic vision test uses a random dot sample, in the same manner as the original version, and achieves stereoscopic vision display of simple test images by use of the cylindrical grid technique, thereby improving reliability of test results. The test is so designed that by properly selecting the dot density, target size, and the parallel axis of stereoscopic vision, even if the card is slightly moved or tilted, the target is almost unrecognizable to monocular vision. For the test to be independently implemented regardless of ages and culture areas, simple and easy-to-understand targets are basically placed. For example, FIG. 11($a$) shows a postcard-size card provided with test figures each consisting of random dot patterns. Herein, targets are not visible with monocular vision. However, with stereoscopic vision, as schematically shown in FIG. 11($b$), three-dimensional stereoscopic vision targets included as submatrixes become visible.

When the subject was judged that he/she has stereoscopic vision, the monocular refractive value is further determined for both eyes. In this case, the prerequisite for subsequent steps is that the monocular corrected visual acuity is at least 0.63.

(S2 Visual Target Display Step)

In this step, visual targets are displayed on the display means 5*a*. In this embodiment, the initial state is the state where a subject who has fixation disparity perceives the visual targets as being shifted in the vertical direction although they are in alignment with each other on the display means 5*a*. Then, a visual target for the left eye and a visual target for the right eye are displayed to the subject wearing 3D spectacles 5*b*. Obviously, each image certainly includes a visual target. Synchronization of image display on the display means 5*a* where visual targets for both eyes are shown and the image display on the 3D spectacles 5*b* is as stated above.

The selection means 5*c* provides an examiner a selection menu of various functions on the apparatus 42 for examiner. By doing so, it is possible to select functions for far distance display on the computer equipped with a screen 43 or functions for near distance display on the apparatus 41 for subject. Those functions include the determination of visual acuity, determination of refraction, test figures used for common optometry for binocular testing, and the aforementioned test figures of this embodiment.

Selection of test figures for the same testing including the test figures of this embodiment is provided for the subject as a function for near distance display on the apparatus 41 for subject. And, the results are complemented by commonly-used near distance visual acuity examination.

The apparatus 42 for examiner, a tablet PC or a laptop for example, is used to remotely control the examinations. By doing so, it is possible to control interactive examination steps, for example, switching from far distance display to near distance display and continuous implementation of various examination procedures.

(S3 Visual Target Movement Step)

In this step, a subject moves a visual target for the left eye and/or a visual target for the right eye by operating the input means 5*d*. In this embodiment, an example will be described in which by moving either one or both visual targets, the subject perceives the visual targets as being aligned, but on the display means 5*a*, the visual targets are out of alignment in the vertical direction. This operation is also referred to as "centering".

The apparatus 42 for examiner is operated by an examiner, and the examiner is guided by the instructions issued by software and obtains the instructions by audio output, for example, coming through the display or headphones.

Figure 6:
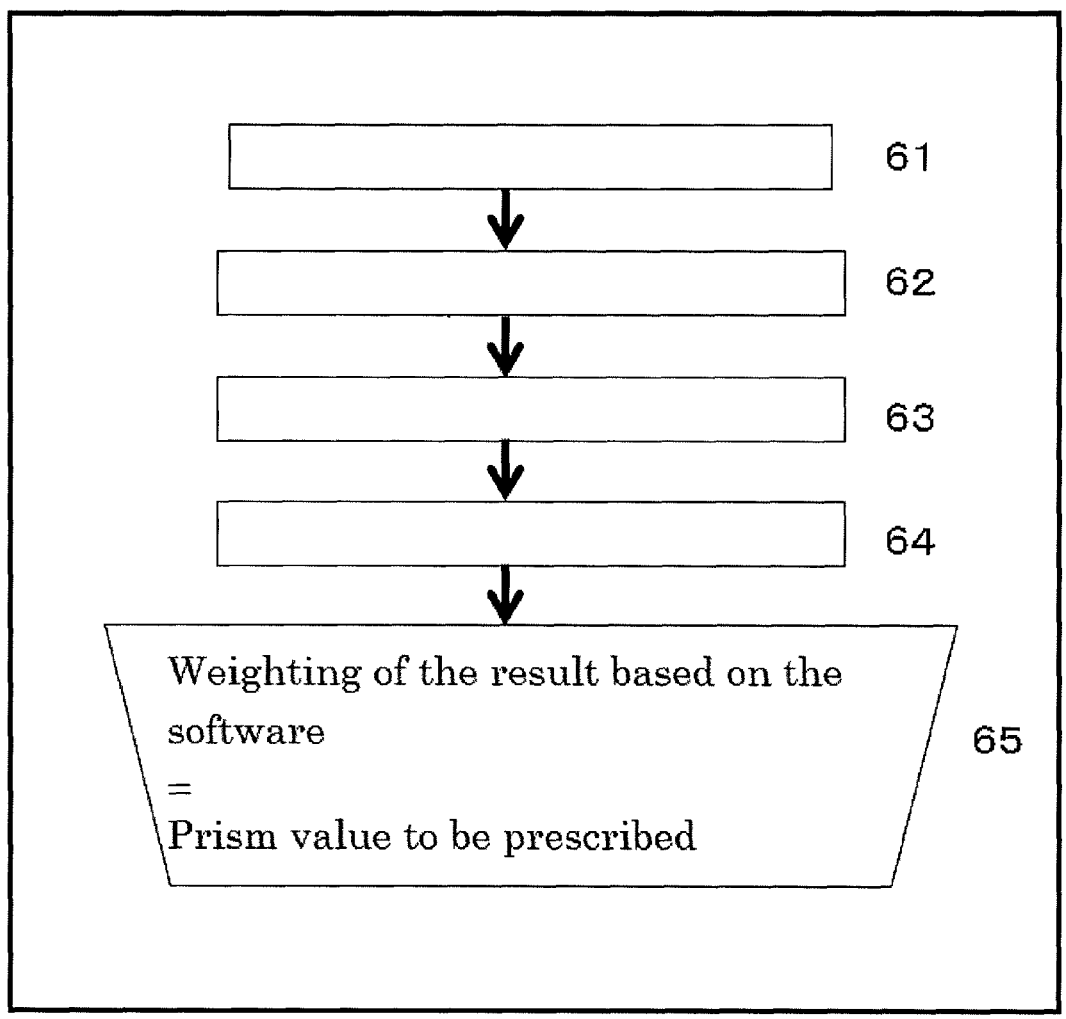
FIG. 6 is a schematic flowchart showing the steps of measuring fixation disparity.

FIG. 6 shows the outline of the method for measuring the direction of the subject's visual fixation line by use of the test figure. This method mainly consists of four steps 61 to 64. In the first step 61 of this method, a prism for conducting the centering in the vertical direction for far distance display is determined. First, an examiner place a measurement lens provided with a predetermined refractive value in the trial frame, and the subject wears the trial frame. For example, the test figure 50 (FIG. 5(a)) for vertical fixation disparity is displayed on the remote monitor. First, the examiner gives an explanation to the subject by saying, "Look at the remote monitor, and see how two horizontal lines 51 and 52 (nonius lines) are placed, and let me know it." When the height of those lines is not the same, the subject uses the apparatus 41 for subject to adjust the lines so that those lines will be perceived to be aligned. The shift of the lines is shown in FIG. 9. FIG. 9 shows the test figure showing the situation where the fixation disparity amount is being calculated.

When the subject adjusts the shift of the nonius lines (e.g., the shift in FIG. 9) and the subjectively-perceived matching state (e.g., the state where nonius lines are in alignment with each other in the vertical direction) is created, the shift is calculated as binocular secession in minutes (angles) according to the following equation:

$$\arctan(\theta) = d/\text{observation distance (unit: meter)} \quad \text{(Equation 9)}$$

where, $\theta$ represents a fixation disparity amount (unit: minute), and d represents a shift amount (unit: meter).

The direction of the shift of the nonius lines adjusted by the subject indicates the state where there is no fixation disparity on the binocular vision, or the state where the shift has been adjusted to the test distance without an error (see FIG. 2(b)), or the state of inward deviation=eso FD (see FIG. 2(a)) or outward deviation=exo FD (see FIG. 2(c)).

For example, in the case of inward deviation (eso FD), the subject adjusts the upper line by moving it to the left relative to the lower line. This direction is evaluated as a positive FD value and calculated according to (equation 9) and expressed in minutes (angles).

For this reason, the apparatus 41 for subject is equipped with an appropriate adjustment apparatus, for example, a mouse, joystick, keyboard, knob, adjustment slider, or contact sensing film of the screen (touch screen). By using the adjustment apparatus, it is possible to move both horizontal lines 51 and 52 (FIG. 5(a)) continuously. In the same manner, both vertical lines 21 and 22 in FIG. 5(b) can also be moved continuously.

In one embodiment, it is possible to dynamically move the lines by use of a physical keyboard or a touch screen keyboard. Operating the key for a short period of time will move a line by a step of 0.5 minute (angle), and as the key operating time increases, the line can be moved by a larger step of 1 to 20 minutes (angle). Furthermore, lines 51 and 52 can also be moved automatically, continuously, or in a step-by-step manner.

The procedure for conducting the centering or adjustment of the horizontal lines is completed by a signal made by the subject indicating that the aforementioned criteria have been satisfied (i.e., the horizontal lines are aligned in the horizontal direction). Therefore, the apparatus 41 for subject may be provided with, for example, an area on the touch screen or an area for clicking a mouse, and the signal may be transmitted from these areas. This signal simultaneously selects a specific parameter, which is the shift between the lines 51 and 52.

Figure 8:
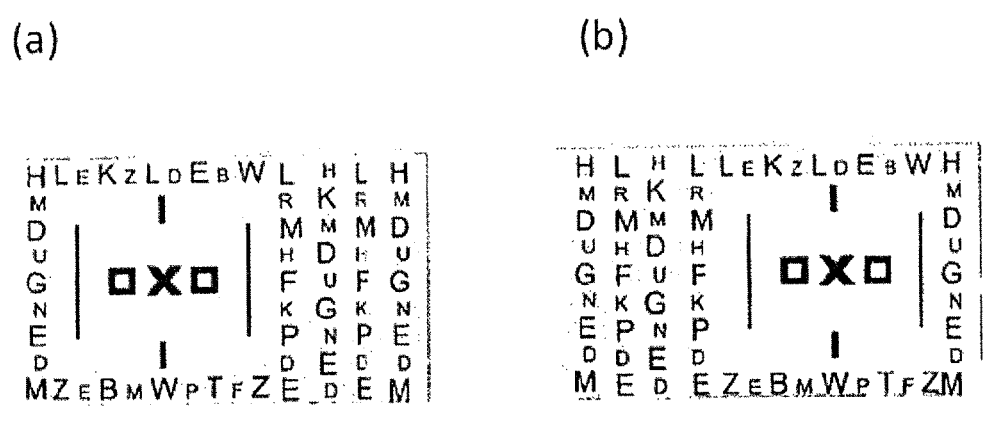

The aforementioned measurement is conducted a plurality of times. For example, when measurement is conducted twice, the test figure is dynamically and alternately displayed on the right half or left half side of the monitor after individual judgment has been made. This example is shown in FIG. 8. FIG. 8 shows the situation where a test figure is placed at the front of the background image provided with a plurality of visual targets for visual fixation. FIG. 8(a) shows the situation where the test figure is displayed on the left side of the display means 5a in the first measurement; and FIG. 8(b) shows the situation where the test figure is displayed on the right side of the display means 5a in the second measurement.

(S4 Fixation Disparity Amount Acquisition Step)

As the result of the operation by means of the input means 5d, the display means 5a shows the situation where the upper and lower visual targets are out of alignment. This shift amount is automatically calculated. Then, from the distance between the subject and the display means 5a, a fixation disparity amount (unit: angle) is calculated. The calculation method is as stated in the previous step.

After a fixation disparity amount in the horizontal direction has been measured, a fixation disparity amount in the vertical direction is measured by use of the method described in S1 to S4. Obviously, a fixation disparity amount in the vertical direction may be measured before the fixation disparity amount in the horizontal direction is measured; and as described in FIG. 5(b) and FIG. 6 of patent document 1, both measurements may be simultaneously conducted.

Then, the aforementioned two measurements are conducted for both far vision and near vision. That is, the fixation disparity amount in the horizontal direction and the fixation disparity amount in the vertical direction are measured for far vision, and the fixation disparity amount in the horizontal direction and the fixation disparity amount in the vertical direction are also measured for near vision.

(S5 Transmission Step)

In this step, the fixation disparity amount obtained by the fixation disparity amount acquisition step (S4) is transmitted from the order-placing computer 2 to the calculation part 7 of the order-receiving computer 3.

(S6 Prism Prescription Value Calculation Step)

In this step, the calculation part 7 calculates an aligning prism (prism prescription value) based on the fixation disparity amount. The specific calculation method is as stated in "5-B-a) Calculation part 7".

Thus, a series of steps as to the acquisition of the aligning prism are completed. After that, the aligning prism is incorporated into spectacle lens design data. The method of incorporating the aligning prism into design data may use a known method in itself. After that, the design data is transmitted to a spectacle lens processing machine, thereby producing a spectacle lens.

9. Advantageous Effects of this Embodiment

Advantageous effects of this embodiment are to solve the problem to be solved by the present invention and the problems described in <4. Problems regarding fixation disparity measurement other than the problem to be solved by the present invention>. In addition, the following advantageous effects can be obtained.

First, in this embodiment, the degree of fixation disparity is objectively detected as much as possible, and the degree of fixation disparity is detected as a distance (fixation disparity amount) on the display means 5a. Therefore, unlike conventional technology, it is possible to accurately detect the degree of fixation disparity.

Moreover, by detecting a fixation disparity amount of the visual targets on the display means 5a after the direction of the shift has been identified, it is certainly possible to determine whether the subject has fixation disparity or not, and it is also possible to make the degree of fixation disparity into data as a fixation disparity amount and transform the fixation disparity amount into an aligning prism provided for a spectacle lens. As a result, it is possible to provide a spectacle lens capable of effectively correcting fixation disparity of the subject.

Furthermore, as to a specific configuration of the display means 5a, a known 3D display may be used. Therefore, when introducing a prism prescription value acquisition system 1 according to this embodiment, it is not necessary to purchase a new apparatus. As a result, expenses for the prism prescription value acquisition system 1 can be held down.

Furthermore, in this embodiment, the procedure for transforming the fixation disparity amount into the aligning prism is guided and supervised by software. Use of the software makes it possible to display the aforementioned newly-developed test figures, for the subject to interactively participate in the measurement, and for the examiner to be guided through usage guidance.

Moreover, according to a preferred embodiment, it is possible for the subject to interactively move, by using an electronic apparatus (e.g., tablet PC), components of the test figure, such as nonius lines, so that those lines will subjectively be perceived as being accurately located at the center (e.g., in alignment with the vertical line or the horizontal line). The centering operation of the test lines are repeated many times. Interactively moving the components of the test figure helps significantly accelerate the measurement procedure.

Furthermore, by interactively moving the components of the test figure, it is possible to reduce the possibility of errors in the communication with the examiner; consequently, even when the examiner is not so skillful, erroneous results can be avoided significantly.

In one embodiment, the control signal is designed to continuously change parameters. By doing so, especially accurate measurement of the direction of the visual fixation line (fixation disparity) becomes possible. This is because as the result of components of the test figure, such as locations, being continuously changed by the subject, it is possible to accurately specify the point at which predetermined criteria are satisfied, for example, the point at which both nonius lines are in vertical alignment. This method is similar to the way of manually adjusting the focus of a projector or a camera. Furthermore, the control signal is designed to change parameters as to the first step width and the second step width. Due to various different step widths, the parameter value that satisfies the predetermined criteria is roughly estimated at the beginning. Then, according to the smaller step width of the two step widths, the desired parameter value is accurately detected.

As stated above, according to this embodiment, it is possible to acquire an aligning prism necessary for correcting fixation disparity by means of a spectacle lens in a simple, quick, and accurate manner.

10. Modification Examples

The present invention is not intended to be limited to the contents of the aforementioned embodiment, and changes can be made as needed without departing from the technical concept of the present invention. Also, the following modifications may be properly combined.

(Judgment Part 8 for Judging Whether a Fixation Disparity Amount is Equal to or Less than a Predetermined Angle)

In the aforementioned embodiment, there is description such that when a fixation disparity amount of the subject is equal to or less than a predetermined angle (e.g., 4 minutes), the calculation part 7 preferably conducts the aforementioned calculation. In association with this, a judgment part 8 for judging whether the fixation disparity amount is equal to or less than the predetermined angle may be provided separately for this embodiment. For example, when the fixation disparity amount is 4 minutes or less, the judgment part 8 issues an instruction to a control means so that the calculation part 7 conducts the aforementioned calculation. On the other hand, when the fixation disparity amount is more than 4 minutes, an aligning prism will be obtained by using a system, referred to as an "expert system", which will be described in [Embodiment 2]. By doing so, it is possible to accurately acquire an aligning prism regardless of the condition where the fixation disparity amount is equal to or less than a predetermined angle. Details will be described later in [Embodiment 2].

(Installation Location of Each Component)

In the aforementioned embodiment, description was made as to the case where either the order-placing computer 2 or the order-receiving computer 3 is equipped with the aforementioned components. On the other hand, the aforementioned components are not necessarily located in the order-placing computer 2 or the order-receiving computer 3. To provide an example, the display means 5a and the input means 5d do not have to be located in the order-placing computer 2 installed in an eyeglass shop. For example, the display means 5a and the input means 5d may be disposed in an eye hospital, and the result (fixation disparity amount) may be transmitted to an eyeglass shop and then transmitted from a terminal (order-placing computer 2) installed in the eyeglass shop to an order-receiving computer 3 equipped with a calculation part 7. However, it is more preferred and easy that a subject who will become a customer conducts operations regarding the locations of the visual targets in the eyeglass shop and the result will be directly transmitted to the order-placing computer 2.

Embodiment 2

Hereinafter, examples other than embodiment 1 will be described. The aforementioned modifications may be incorporated into the following embodiments as needed. Furthermore, in the following embodiments, examples of the prism prescription value acquisition system 1 will be described; however, obviously, those examples may also be applied to a prism prescription value acquisition method, a prism prescription value acquisition apparatus, and a prism prescription value acquisition program. Contents that are overlapped with those of embodiment 1 will be omitted herein.

<Expert System>

In this embodiment, the "judgment part 8" described in <10. Modifications examples> is applied to the contents of embodiment 1. When a fixation disparity amount is larger than a predetermined angle, a system referred to as an "expert system" is used to obtain an aligning prism. Hereinafter, description will be given based on the prism prescription value acquisition method according to embodiment 1. Herein, the use of the expert system makes it possible to acquire an aligning prism with a required time of approximately 10 minutes.

First, up to (S4 Fixation disparity amount acquisition step), contents are as described in embodiment 1; however, subsequent contents are different. As for this point, description is provided in FIG. 13 and FIG. 14.

(S7 Judgement Step)

In this step, it is judged whether or not a fixation disparity amount is equal to or less than a predetermined angle. When the fixation disparity amount is 4 minutes or less, the judgment part 8 issues an instruction to the control means so that the calculation part 7 will conduct the aforementioned calculation. In that case, the procedure will proceed to (S5 Transmission step) as described in embodiment 1. On the other hand, when the fixation disparity amount is more than 4 minutes, a system referred to as an "expert system" is used to obtain an aligning prism.

(S8 Aligning Prism Acquisition Step by an Expert System)

Outline of the expert system is as follows:

With software, the display of the test figures described in embodiment 1, bi-directional use by subject, and usage guidance for examiner are made possible. This measurement method is so designed that by means of the expert system using software, the examiner guides and monitors the operations.

Such an overall system may include a second order-placing computer 2' in addition to the aforementioned apparatus for measuring the direction of the visual fixation line of the subject. In this case, the examiner operates the second order-placing computer 2' and thereby controls the entire measurement procedure. For example, every time a measurement is conducted, the software indicates the trial lens provided with an exact prism value so as to be installed in the trial frame. That is, it is not necessary to refurbish trial lenses or trial frames just because the expert system is introduced; normally-used trial lenses and trial frames can be used continuously.

In the expert system, at the beginning, as standard optometry examination, subjective refraction measurement for far distance and near distance should be completed.

Measurement of other visual functions should also be conducted as standard optometry examination, and visual acuity should be 0.63 (20/32) or higher for both eyes.

Upon use of the expert system, result of the examination using this embodiment and using the improved random dot stereo card based on the conventional method (e.g., FIG. 11(*a*) and FIG. 11(*b*)) should be positive and the subject has stereoscopic vision. That is, in the following examples, a subject can stereoscopically recognize test patterns hidden in the card. This will make it possible to accurately assume and confirm that the subject has normal binocular visual acuity and does not have strabismus.

Figure 7A:
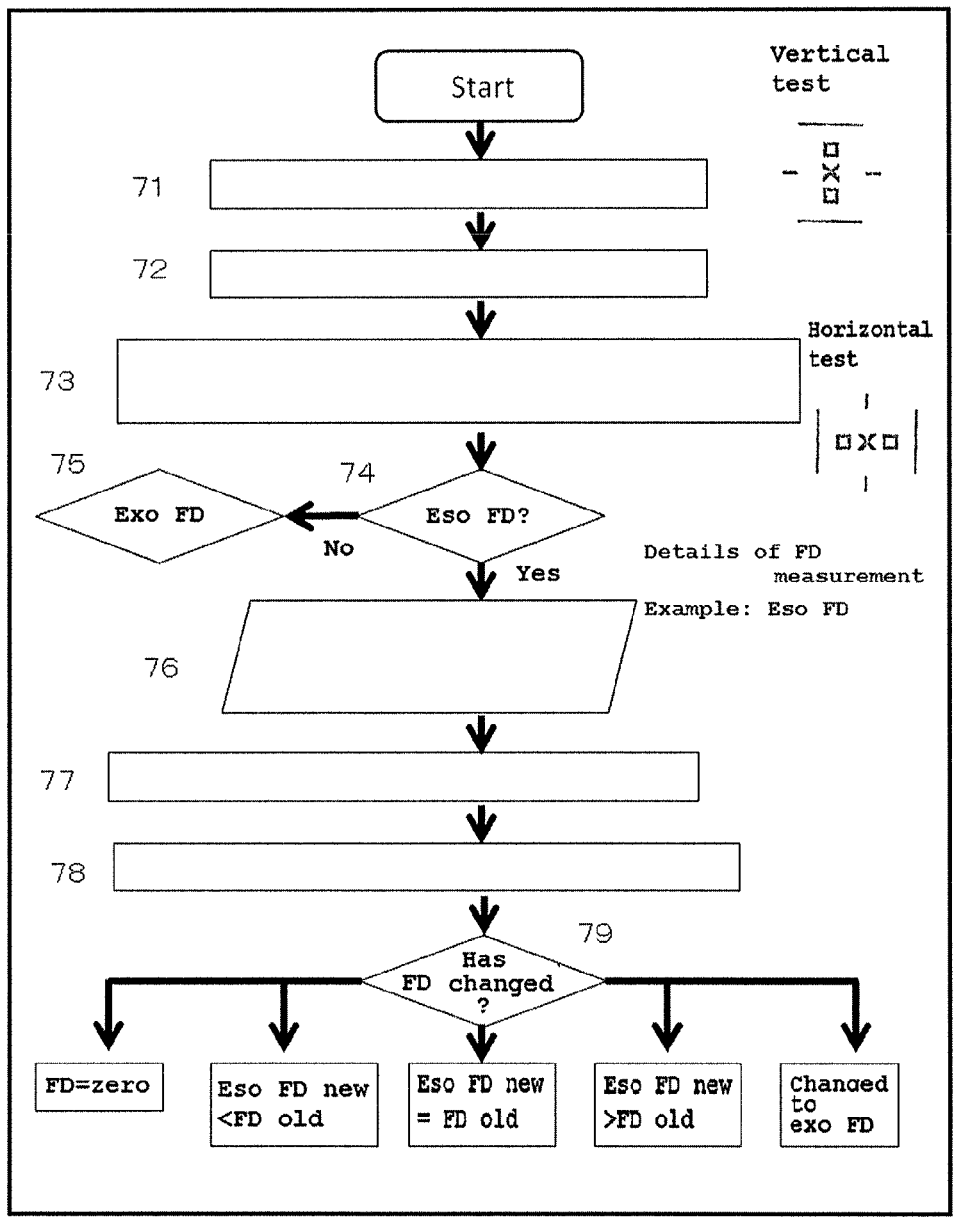
FIG. 7A is a schematic flowchart (part 1) showing the steps taken when eso fixation disparity is measured.
Figure 7B:
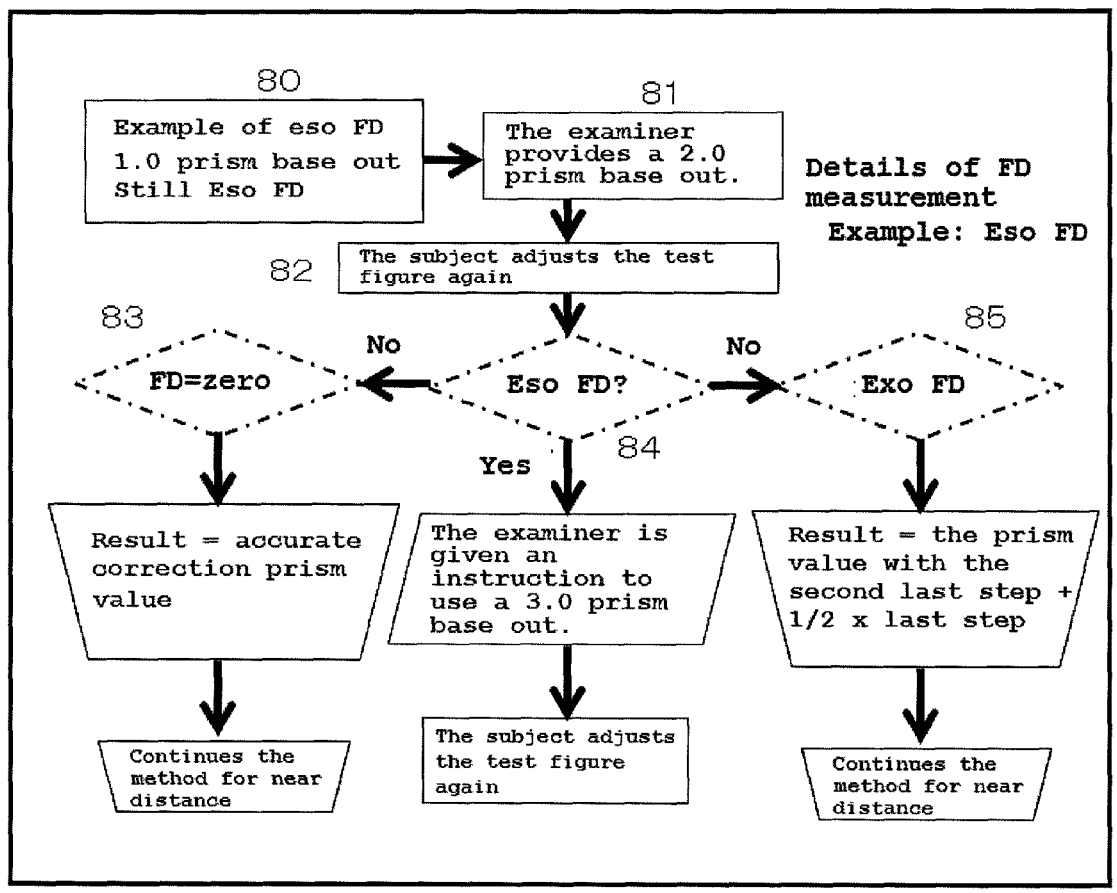
FIG. 7B is a schematic flowchart (part 2) showing the steps taken when eso fixation disparity is measured.

On the basis of the above, in this step, the expert system described below is used. Hereinafter, description will be given with reference to previously shown FIG. 6, and FIG. 7A and FIG. 7B showing the schematic flowchart of the steps to measure eso fixation disparity.

After the first operation (partial step 71) of two centering operations (measurement of the fixation disparity amount), as the result of the measurement, the examiner is given instructions, through the display of the apparatus 42 for examiner or audio output, on a prism value and a basal direction (upward or downward) provided for the trial lens for each eye to be used for the second operation (partial step 72). The examiner incorporates this prism value (hereinafter, referred to as a "correction prism"), for example, upward 0.5Δ in the basal direction for the right eye into a trial lens and mount the lens to the trial frame. Then, subsequent measurement operations are conducted, and then a prism value will be indicated. According to the instructions issued by the expert system, the value of the correction prism and the basal direction are obtained, and this procedure will be repeatedly conducted until the next step is required.

It is reasonable that the following components normally used for optometry be additionally used: trial frames, trial lens box equipped with spherical power and cylindrical power lenses, and a certain number of prism lenses. Trial lenses provided with prism diopter (Δᵗ) of 0.5/1.0/2.0/3.0/4.0/5.0/6.0 should be prepared.

In the second step 62 of this method, the correction prism for far distance display is determined in the horizontal direction. Therefore, the test figure 55 is used for the measurement of horizontal fixation disparity (FIG. 5(*b*)), and the fixation disparity is corrected by the prism base in or prism base out.

In the partial step 73, the test figure for horizontal fixation disparity (FIG. 5(*b*)) for far distance display is displayed on the computer equipped with a screen 43. When a subject perceives this test figure as being out of alignment in the horizontal direction, as described in relation to the first step 61 in FIG. 6, the subject uses the apparatus 41 for subject to adjust the test figure. Centering or adjustment of the horizontal line of the test figure is completed by a signal made by the subject indicating that the aforementioned criterion has been satisfied (i.e., the vertical lines are aligned in the vertical direction). This signal simultaneously selects a specific parameter, which is the shift between the lines 51 and 52. This centering operation is conducted twice, and in each centering operation, the test figure appears on the right or left side of the monitor. When the test figure appears on the right side in the first centering operation, the test figure appears on the left side in the second centering operation, or vice versa. This measurement corresponds to measurement A in this specification. As explained 5-B-a) calculation part 7, in order to confirm the reliability of the measurement itself of the fixation disparity, the measurement is performed twice under the same condition. It is preferable to confirm whether or not a difference between the fixation disparity amount obtained by far distance and the fixation disparity amount obtained by near distance, is within a defined value. At this time, as described in 5-A-a 1) displayer 5*a*, when a plurality of measurements are performed, a location of visual target on the display is preferably changed in each measurement, in a front surface of a background image on the display. The measurement procedure of such two times of measurement of fixation disparity is included in above-mentioned first measurement procedure.

After the first operation of two centering operations, as the result of the measurement, the examiner is given instructions, through the display on the apparatus 42 for examiner or audio output, on a prism value and a basal direction (upward or downward) for each eye (partial step 76). The examiner uses this prism value, for example, 1Δ upward from the basal direction, for measurement spectacles (partial step 77). The same procedure is conducted for the case where a subject has exo fixation disparity (partial steps 74 and 75). Then, subsequent measurement operations (corresponding to measurement B in this specification) are conducted, and a prism value will be indicated again (partial step 78). After that, how the newly obtained prism value is different from the previous prism value is checked, and based on that, how this method should be proceeded will be checked (partial step 79).

In subsequent partial steps shown in FIG. 7B, for example, if eso fixation disparity is still present after the prism with a prism value of 1Δ has been used in partial step 77, another method will be indicated (partial step 80). At this time, the trial frame equipped with a trial lens with a prism value (correction prism) of 2Δ is used (partial step 81). The subject adjusts the test figure again (partial step 82). When fixation disparity is zero, which means that the subject did not adjust the test figure, a prism value will be determined (partial step 83). When eso fixation disparity is present, operation will be continued by providing a higher prism value (partial step 84). When exo fixation disparity is present, the resulting prism value is an average value of the last two prism values.

In the third step 63 and fourth step 64 of this method, the correction prism in the vertical direction or horizontal direction is determined for near distance display.

In this case, in the same step as far distance display (steps 61 and 62), the same test figure is used; however, this time, the test figure is displayed for near vision on the apparatus 41 for subject remotely operated by the subject.

According to the aforementioned calculation, aligning prisms (vertical and horizontal) that correspond to far distance display are obtained, and separately, aligning prisms (vertical and horizontal) that correspond to far distance display are also obtained. That is, four aligning prisms can be obtained. Therefore, far distance result and near distance result are evaluated at the end, and weighting is implemented according to the actual experience using the Haase method and the principles obtained based on the research result of the Mallett and Sheedy method. As a result, prism values (vertical and horizontal) to be prescribed can be obtained. Those prism values are encoded and can be transmitted via a normally-used ordering system of a spectacle lens manufacturer (step 65). As explained 5-B-a) calculation part 7, it may be measured four aligning prisms. It is preferred.

A certain number of case examples indicate that according to the conventional method, correction by a correction prism results in a very large prism value, and very thick lenses are required for correction spectacles, or surgery of extraocular muscle is required. Therefore, this method limits the prism value for optometry correction to a maximum of 6Δ. If this still does not achieve centering of the test figure, the software recognizes that and indicates that the value is not within the predetermined correction range and the subject needs diagnosis by an expert.

Furthermore, according to a preferred embodiment, by combining a measurement apparatus for displaying the test figure with the software-based evaluation, the degree of prism power for correction is determined. The examiner is given information by the software on how to create the examination procedure, and the subject responds by the input into the apparatus. Finally, the result is encoded and a spectacle lens manufacturer can apply the data to the spectacle lens.

<More Preferred Expert System>

When two vertical lines are perceived as being in vertical alignment without shifting to the left or right by means of the prism incorporated into the above-mentioned trial frame for optometry, the prism incorporated into the trial frame for optometry can be obtained as the correction prism value for fixation disparity in the vertical direction and in the horizontal direction at the far distance display and the near distance display. However, this is the prism value obtained when the subject wears the measurement spectacles having a trial frame with a real trial lens and fixation disparity has been eliminated. Therefore, a correction prism value to be obtained varies depending on the degree of steps of the prism value of the prepared trial lenses. Since prism lenses for optometry have been made with a step of 0.25Δ (prism diopter), it is not possible to obtain a correction prism of a value smaller than 0.25Δ.

Figure 10:
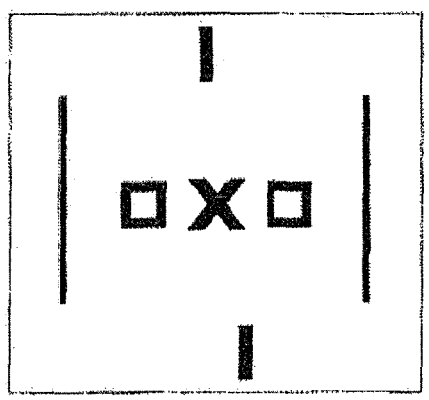
FIG. 10 shows test figures showing the situation where nonius lines are being moved while fixation disparity is being measured.
Figure 10:
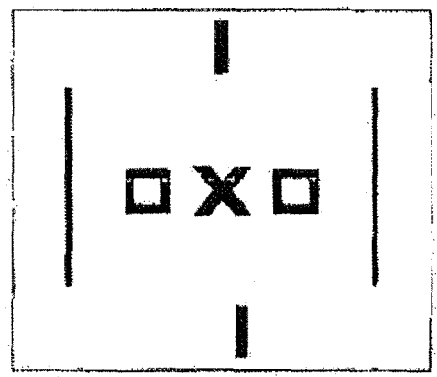

For example, when eso FD is present, a correction prism outward from the basal direction is given to neutralize error. Based on the first adjustment by the subject, this system sends the examiner a message indicating that in the first step of this example, a correction prism of 1 cm/m outward from the basal direction should be used for measurement spectacles. This is shown, for example, in FIG. 10. The test figure on the left side in FIG. 10 shows the adjustment of nonius lines by the subject which is conducted at the end of the first examination step. The test figure on the right side in FIG. 10 shows the adjustment of nonius lines by the subject which is conducted after the prism has been incorporated into the measurement spectacles at the end of the second examination step. This can be compared with the situation in the case of vertical deviation.

Next, the subject wears the trial frame provided with a trial lens incorporating the correction prism. Then, the shift of the lines subjectively adjusted again is measured as an FD value. Subsequently, according to the change of the FD value, the expert system makes decisions on the next step. Only in a few cases, it is expected that FD is accurately corrected to zero by a rough prism step of 0.5Δ or a grading of 1Δ. However, excessive correction by a predetermined prism step occurs more frequently, which is indicated by the inversion of the FD direction. Interchange of the positive and negative signs is used to calculate the prism for centering as an average value so that it can be compared with the determination of the fixation disparity curve presented by Sheedy.

Other than the above-mentioned method of obtaining a correction prism for correcting fixation disparity, the following method is also possible.

The expert system equipped with the software is designed to issue instructions to the examiner indicating that the prism amount to be provided for the trial frame should be a rough step of 1.00 prism diopter. Then, by means of the prism indicated by the software, it is preferred that the correction prism value which corrects fixation disparity to zero be obtained by proportionally distributing, before and after the time when position alignment directions of two lines of the test pattern for fixation disparity have been reversed, the respective fixation disparity amounts obtained from the position alignment amounts of before-and-after two lines and the values of the two prisms provided for the before-and-after trial frame for optometry.

The following equation indicates the way of proportional distribution:

$$AP=P2-(P2-P1)*FD2/(FD2-FD1) \quad \text{(Equation 10)}$$

AP represents the prism amount (unit: prism diopter) of the aligning prism.

FD1 represents the fixation disparity amount (unit: angle) immediately before the direction of fixation disparity is reversed.

FD2 represents the fixation disparity amount immediately after the direction of fixation disparity has been reversed, and the sign of FD1 and FD2 is such that it is positive when the direction of fixation disparity is outward and negative when it is inward.

P1 represents the prism amount immediately before the direction of fixation disparity is reversed.

P2 represents the prism amount immediately after the direction of fixation disparity has been reversed.

For example, when fixation disparity is measured with a prism of 1.00 prism base in provided for either the right eye or the left eye, the fixation disparity amount is 0.7 minute outward; and when the provided prism is changed to 2.00 prism base in and measurement is conducted, the fixation disparity amount is 0.4 minute inward; then when the direction of fixation disparity is reversed, an aligning prism can be obtained from the prisms and the fixation disparity amounts by using the following (equation 10).

$$AP=2.00+(2.00-1.00)*(-0.40)/((-0.4)-0.70)=1.64 \quad \text{(Equation 11)}$$

Thus, an aligning prism can be obtained with an increment of 0.01 prism diopter.

In this method, trial lenses with a prism used for the procedures before the aligning prism is obtained are prepared with an increment of 1.00 prism diopter. Therefore, the number of times trial lenses are replaced before the aligning prism is obtained is reduced, thereby reducing the measurement time. Furthermore, the correction prism amount thus obtained can be obtained by proportional distribution. Therefore, in spite of an increment of 1.00 prism diopter, it is possible to obtain an aligning prism with an increment of 0.01 prism diopter.

Incidentally, according to the aforementioned embodiment, as stated in the above "Advantageous Effects of Invention", it is possible to obtain an accurate aligning prism. However, subsequently, it is considered that each eyeglass shop asks each spectacle lens manufacturer to make the spectacle lens. If so, even if the eyeglass shop has obtained an accurate aligning prism, depending on spectacle lens manufacturers, the aligning prism is not accurately incorporated, which results in a low-quality spectacle lens. If that happens, the purchaser of the spectacle lens, who was the subject, ends up purchasing a spectacle lens which does not eliminate fixation disparity although the aligning prism for correcting fixation disparity was accurately obtained.

For this reason, an encoded value (e.g., a form of a bar code) is outputted as the result of having obtained an accurate aligning prism by using the aforementioned embodiment. The use of the information included therein is not allowed without using the corresponding key. That is, even if an eyeglass shop has obtained a correction prism for correcting fixation disparity by using the aforementioned embodiment, the correction prism has been encoded and is unrecognizable to arbitrary spectacle lens manufacturers. By doing so, it is possible to allow an order to be placed with only a qualified spectacle lens manufacturer who has the best possible ability to correct fixation disparity and superior lens technique.

To integrate the aforementioned components and software-based methods into an expert system is also a novel matter. This is for the first time embodied by use of a currently-available electronic apparatus. The feature is that existing methods have been integrated and improved to thereby avoid conventional disadvantages. In addition, provision of the expert system is expected which can be integrated into a practically-utilized configuration, offered at a marketable price, and is easy-to-use as much as possible.

By use of an expert system related to the measurement and correction of the eye axis error (fixation disparity), direct and interactive communication between the examiner and the subject is possible. This is as described in the aforementioned embodiment. If there is no communication between the examiner and the subject and the system is completely automated, unnatural visual stimulation could possibly occur. Because of this, unreliable result is considered to occur. On the other hand, the expert system does not have such a disadvantage. This is because this embodiment can be installed indoor in the same manner as the conventional configuration for determining an aligning prism and can also use conventional measurement spectacles.

In this embodiment, description is given of the example where a judgment part 8 is provided for embodiment 1 in which a fixation disparity amount is transformed into an aligning prism, and where an expert system is also combined. On the other hand, the expert system is an invention that can stand alone without being combined with embodiment 1. Problems to be solved in that case are as described below.

From non-patent document 1, the inventor of the present invention has acquired findings that just because a fixation disparity amount is simply converted to prism diopter based on the distance between visual targets and a subject does not follow that the amount will become an aligning prism to be eventually provided for a spectacle lens. This leads to the fact that since the relationship between the "prism amount converted from a fixation disparity amount based on the distance between visual targets and a subject" and the "aligning prism" significantly varies among different individuals, it is not possible to obtain an accurate aligning prism from the fixation disparity amount by means of calculation. If so, after all, even if a fixation disparity amount is obtained, there is no way to utilize it, and as in the same manner as the conventional method, to find a prism amount necessary for eliminating fixation disparity, there is no other way than painstakingly obtaining an aligning prism by use of a trial lens.

However, when trial lenses are prepared with 0.25Δ increments, if, for example, a subject needs a trial lens having a prism prescription value of 0.35Δ, it is not possible to provide an appropriate spectacle lens for the subject; consequently, the subject's fixation disparity cannot be corrected by means of a spectacle lens.

Accordingly, a main objective of this embodiment is to accurately acquire a prism prescription value necessary for correcting fixation disparity by means of a spectacle lens.

Specific configuration is as described below. Obviously, components described in this specification may be combined with the following configuration or changes may be made as needed.

<Expert System>

This is a prism prescription value acquisition method for acquiring a prism prescription value from a fixation disparity amount indicating the degree at which the visual axis is deviated from the central fovea of the retina when a subject conducts visual fixation of a target, wherein after measurement A of the fixation disparity amount of the subject has been conducted, the subject wears measurement spectacles provided with a predetermined prism amount according to the fixation disparity amount, measurement B of the fixation disparity amount is conducted, and then any one of the following processes 1 to 3 is conducted.

(Process 1) When fixation disparity has ceased to be perceived in measurement B, the prism amount of the measurement spectacles is used as a prism prescription value.

(Process 2) When the subject still perceives fixation disparity even in measurement B and when in measurement B, eso fixation disparity is turned to exo fixation disparity or exo fixation disparity is turned to eso fixation disparity, any one of the following processes (i) to (ii) is conducted.

(i) In measurement A, when the subject doesn't wear measurement spectacles provided with a predetermined prism amount, half of prism value of the measurement spectacles in measurement B is used as a prism prescription value.

(ii) In measurement A, when the subject wears measurement spectacles provided with a predetermined prism amount, the average value of the prism amount of the measurement spectacles in measurement A and the prism amount of the measurement spectacles in measurement B is used as a prism prescription value.

In (ii), average value is applied. But in (i), half of prism value of the measurement spectacles in measurement B is used as a prism prescription value, because prism value in measurement A is regarded as zero.

(Process 3) When the subject still perceives fixation disparity even in measurement B and when in measurement B, either eso fixation disparity or exo fixation disparity remains, the subject wears measurement spectacles provided with a higher power prism than the predetermined prism amount, and the fixation disparity amount is measured again, then the measurement of the fixation disparity amount is repeatedly conducted by increasing the power of the prism provided for the measurement spectacles until the state of (process 1) or (process 2) is achieved.

<More Preferred Expert System>

This is a prism prescription value acquisition method for acquiring a prism prescription value from a fixation disparity amount indicating the degree at which the visual axis is deviated from the central fovea of the retina when a subject conducts visual fixation of a target, wherein after measurement A of the fixation disparity amount of the subject has been conducted, the subject wears measurement spectacles provided with a predetermined prism amount according to the fixation disparity amount, measurement B of the fixation disparity amount is conducted, and then any one of the following processes 1 to 3 is conducted.

(Process 1) When fixation disparity has ceased to be perceived in measurement B, the prism amount of the measurement spectacles is used as a prism prescription value.

(Process 2) When the subject still perceives fixation disparity even in measurement B and when in measurement B, eso fixation disparity is turned to exo fixation disparity or exo fixation disparity is turned to eso fixation disparity, any one of the following processes (iii) to (iv) is conducted.

(iii) In measurement A, when the subject doesn't wear measurement spectacles provided with a predetermined prism amount, prism prescription value is calculated by following formula.

$$AP=P2-P2 \times FD2/(FD2-FD1)$$

(iv) In measurement A, when the subject wears measurement spectacles provided with a predetermined prism amount, prism prescription value is calculated by following formula.

$$AP=P2-(P2-P1) \times FD2/(FD2-FD1)$$

AP represents an amount of prism value (unit: prism diopter) of the aligning prism.

FD1 and FD2 are the fixation disparity amounts before and after eso fixation disparity has been turned to exo fixation disparity, or exo fixation disparity has been turned to eso fixation disparity in measurement B.

The sign of FD1 and FD2 is such that it is positive when the direction of fixation disparity is outward and negative when it is inward.

P1 and P2 are the prism amounts before and after eso fixation disparity has been turned to exo fixation disparity, or exo fixation disparity has been turned to eso fixation disparity in measurement B.

(Process 3) When the subject still perceives fixation disparity even in measurement B and when in measurement B, either eso fixation disparity or exo fixation disparity remains, the subject wears measurement spectacles provided with a higher power prism than the predetermined prism amount, and the fixation disparity amount is measured again, then the measurement of the fixation disparity amount is repeatedly conducted by increasing the power of the prism provided for the measurement spectacles until the state of (process 1) or (process 2) is achieved.

According to this embodiment, it is possible to accurately acquire a prism prescription value necessary for correcting fixation disparity by means of a spectacle lens.

Herein, the expert system is a technique for obtaining an aligning prism based on the fixation disparity amount.

Embodiment 3

In the aforementioned embodiment, description was given of the example where an aligning prism is acquired based on the "fixation disparity amount". In this embodiment, description will be made of the method by which an aligning prism is not acquired based on the fixation disparity amount but an "aligning prism" is directly and easily acquired without measuring the fixation disparity amount. Contents that are overlapped with those of embodiments 1 and 2 will be omitted herein.

Problems to be solved by this embodiment are as follows:

Conventionally, to correct fixation disparity, there is no other way than painstakingly obtaining an aligning prism by use of trial lenses with prisms.

When obtaining an aligning prism by use of a trial lens, the only known technique is that a subject sequentially wears a plurality of trial lenses provided with a prism (e.g., 0.25 prism diopter increments) and that when the subject perceives visual targets, which are displayed individually to right and left eyes, as being located at locations that are aligned, the prism prescription value of the trial lens at that time is adopted. To use this technique, each eyeglass shop has to prepare a large variety of trial lenses. Obviously, it takes time to have each subject wear a variety of trial lenses. Also, when trial lenses are prepared with 0.25Δ increments, if, for example, a subject needs a trial lens having a prism prescription value of 0.35Δ, it is not possible to provide an appropriate spectacle lens for the subject; consequently, the subject's fixation disparity cannot be corrected by means of a spectacle lens.

Accordingly, a main objective of the present invention is to acquire a prism prescription value (aligning prism) required for correcting fixation disparity by means of a spectacle lens in a simple, quick, and accurate manner.

The display means 5a in this embodiment has a function to display an image for the left eye including a visual target (nonius line) and a background image and an image for the right eye including a visual target (nonius line) and a background image. In other words, the display means 5a in this embodiment is a portion capable of displaying an image for the left eye to the left eye and displaying an image for the right eye to the right eye. The visual target (nonius line) for the right eye is only displayed to the right eye. The visual target (nonius line) for the left eye is only displayed to the left eye.

In the above case, a visual target for visual fixation is not provided. Furthermore, the image for the left eye and the image for the right eye can be moved individually. This configuration can reproduce the situation which is the same as the situation where a subject wears a prism lens. That is, when a subject wears a prism lens, for example, in the right eye, the entire visual field perceived by the right eye is shifted inwardly or outwardly. This situation is reproduced on the display means 5a. To do so, the display means 5a displays at least an image for the right eye and an image for the left eye, each image including a background image in addition to a visual target, and background images are so disposed that they are not out of alignment when visual targets are not out of alignment with each other.

An image for the right eye and an image for the left eye are displayed, and each image includes a background image in addition to a visual target (nonius line). The "background image" in this embodiment is, as its name indicates, an image serving as background for the image for the right eye. The background image may show patterns or characters.

Obviously, this embodiment is applicable when the image does not include a background image but includes only a visual target (nonius line); however, in light of the contents described in patent document 1, it is preferred that the image for the right eye and the image for the left eye each include a background image. In this embodiment, an example will be provided regarding that case.

In this embodiment, it is not necessary to obtain the fixation disparity amount based on the results obtained by means of the display of the display means 5a. Eventually, an aligning prism to be incorporated into a spectacle lens will be acquired. Outline is as shown below. First, in two states to be displayed on the display means 5a, the direction of shift is identified and then a shift amount of the locations of the visual targets is acquired. The two states are shown in FIG. 15. FIG. 15 is a conceptual diagram showing the details of the prism prescription value acquisition system in this embodiment. Herein, the two states refer to the states described below.

(State 1)

This is the state in which when a subject with fixation disparity sees, via 3D spectacles 5b, an image for the right eye displayed on the display means 5a with the right eye and also sees an image for the left eye displayed on the display means 5a with the left eye, the subject perceives the images as being out of alignment, but the images for the right eye and the left eye are in alignment with each other on the display means 5a.

(State 2)

This is the state in which when the same subject sees, via 3D spectacles 5b, an image for the right eye displayed on the display means 5a with the right eye and also sees an image for the left eye displayed on the display means 5a with the left eye, the subject perceives the images as being in alignment with each other, but the images are out of alignment on the display means 5a.

That is, in state 1, when viewed with both eyes, on the display means 5a, the vertically-located nonius lines in the image is aligned in the top and bottom direction and visual targets are not out of alignment. And the back ground images which are displayed to both eyes separately are displayed at the same position on the display means 5a. However, the subject who has fixation disparity looks at the display means 5a with both the right eye and the left eye via 3D spectacles 5b, the subject perceives only the vertical nonius lines as being out of alignment. The images except nonius lines are perceived as one image by means of processing by the brain, referred to as fusion.

Contrary to state 1, in state 2, when viewed with both eyes, the subject perceives the vertical nonius lines as being aligned in the top and bottom direction. However, on the display means 5a, the vertical nonius lines are out of alignment in the horizontal direction. And the back ground images which are displayed commonly to both eyes and are displayed separately to each eye are displayed at the shifted position each other on the display means 5a. In this case, the horizontal direction is identified as a "direction of shift".

That is, the shift amount and shift direction of the visual targets (images) on the display means 5a in between state 1 and state 2 correspond to the aligning prism and direction thereof. Then, it is possible to provide the subject with a spectacle lens having an aligning prism (prism prescription value) capable of correcting fixation disparity.

Herein, in this embodiment, by means of the input means 5d, the visual target (nonius lines) and the back ground images for the right eye and the visual target (nonius lines) and the back ground images for the left eye displayed on the display means 5a are moved equally close to or distant from each other. In other words, relative movement of the whole image for the right eye and the whole image for the left eye displayed on the display means 5a are conducted. In the case of this embodiment, this relative movement amount corresponds to the shift amount. Obviously, the half value (e.g., the distance the above-mentioned visual target has been moved) of the scale displayed on the display means 5a in FIG. 2 may be treated as a shift amount. In this embodiment, since it is necessary to acquire an "aligning prism" instead of a "fixation disparity amount", visual targets for visual fixation do not exist, but the entire image for the right eye and the entire image for the left eye are moved. Therefore, in cases where the scale is provided in the image for each eye, as the image for each eye is moved, the scale is also moved accordingly.

Furthermore, in this embodiment, by means of the input means 5d, the image for the right eye including a visual target (nonius line) for the right eye and a background image and the image for the left eye including a visual target (nonius line) for the left eye and a background image are moved equally close to or distant from each other. At the time when it is checked whether the visual targets are out of alignment or not, by conducting relative movement of the background image along with an index, it is possible to accurately acquire a shift amount. The reason is as described below.

When visual targets (nonius line) are not out of alignment, the background image for the left eye and the background image for the right eye are also considered not out of alignment. In the case of this embodiment, when vertically-located visual targets are aligned in the top and bottom direction, the subject clearly sees the background image in the visual field. Even if the subject cannot judge whether the vertical visual targets are aligned in the top and bottom direction or not, if the subject sees the background image clearly, it is possible to regard the vertically-located visual targets as being aligned. That is, the background image for the left eye and the background image for the right eye help the judgment of whether the visual targets are out of alignment or not. In this embodiment, since state 1 is a criterion for the shift amount, it is necessary to accurately grasp state 1. Therefore, by adopting the background image, it is possible for a subject to accurately judge the state where visual targets are not out of alignment, and the state 1 can be accurately grasped, which results in acquiring an accurate shift amount. Then, this shift amount can be converted to an aligning prism by the calculation part 7 based on the distance between the subject and the display means 5a.

Moreover, there is a method for acquiring an aligning prism by using a trial lens provided with a prism and correcting the prism of the trial lens based on the shift amount. This is a technique in which a trial lens is used to grasp a rough range of the aligning prism necessary for the subject and after that, the aforementioned technique is used to acquire an accurate aligning prism. However, since the feature of this embodiment is to acquire an aligning prism without using a trial lens, it is preferred that the trial lens not be used.

Furthermore, for the visual target displayed on the display means 5a to be clearly viewed, it is effective to prevent objects other than the display means 5a from coming into the visual field of the subject. Therefore, it is preferred that the prism prescription value acquisition system be provided with a configuration which shows the display means 5a relatively bright when the display means 5a comes into the visual field of the subject. Specifically, it is preferred that the prism prescription value acquisition system according to embodiment 1 be provided with a light-dark formation part for relatively brightly showing the display means 5a to the subject.

The light-dark formation part described herein is the portion that enables the subject to perceive an image (visual target as well) as being extremely bright in the visual field. Hereinafter, a specific example of the light-dark formation part will be described.

First of all, there are cases in which the light-dark formation part is the 3D spectacles 5b equipped with a visible-light shielding function. These 3D spectacles 5b can be sunglasses equipped with an active shutter function. If a subject wears the sunglasses and makes use of the prism prescription value acquisition system, only the display means 5a comes into the visual field of the subject. Also, it is effective to increase the intensity of backlight of the display means 5a higher than the conventional one.

By doing so, the subject perceives the display means 5a brighter than other portions, and only the display means 5a comes into the visual field of the subject. As a result, the subject can see well the visual target displayed on the display means 5a, and it is possible to accurately acquire a shift amount and accurately acquire a prism prescription value. Furthermore, it has been clearly proven through the research by the inventor that if an object other than the display means 5a comes into the subject's visual field, the prism prescription value for far vision is greatly affected. Therefore, the aforementioned technique is significantly effective when acquiring a prism prescription value for far vision.

According to this embodiment, it is possible to objectively acquire an aligning prism by grasping a shift amount of the images on the display means 5a. That is, it is possible to acquire an aligning prism without needing a trial lens. Therefore, burden on the eyeglass shops and subjects can be greatly reduced. As a result, it is possible to acquire an aligning prism necessary for correcting fixation disparity by means of a spectacle lens in a simple, quick, and accurate manner.

Furthermore, the method according to this embodiment 3 may be used as a means for confirming the vision of the subject by means of the aligning prism acquired by the aforementioned embodiment 1 or embodiment 2. By shifting the locations to display images presented to the entire visual field of the left eye and the right eye according to the method of embodiment 3 according to the amount of aligning prism obtained by embodiment 1 or embodiment 2, it is possible to confirm that the subject can see without having fixation disparity. In this method, without using a prism lens, it is possible to easily confirm that the subject can see without having fixation disparity as the result of the correction of the fixation disparity by means of the aligning prism.

Moreover, the configuration incorporating this embodiment is as follows:

This is a prism prescription value acquisition system for acquiring a prescription value for correcting fixation disparity of a subject's right eye and left eye by means of a spectacle lens, comprising a prism prescription value acquisition part for acquiring a prism prescription value for a spectacle lens for a subject having fixation disparity, the prism prescription value being calculated based on the shift amount and shift direction of the images on the display means, between the state in which the subject sees an image for the right eye displayed on the display means with the right eye via 3D spectacles, and when it sees an image for the left eye displayed on the display means with the left eye, the subject perceives the images as being out of alignment, but the images are not out of alignment on the display means; and the state in which the subject sees an image for the right eye displayed on the display means with the right eye via 3D spectacles, and when it sees an image for the left eye displayed on the display means with the left eye, the subject perceives the images as being aligned, but the images are out of alignment on the display means.

Herein, the image includes a visual target and a background image.

Moreover, a part of the configuration of this embodiment may be applied to embodiments 1 and 2.

REFERENCE SIGNS LIST

1 Prism prescription value acquisition system
2 Order-placing computer
3 Order-receiving computer
4 Communication line
5 Measuring part
5a Display means
5b Accessory device (3D spectacles)
5c Selection means
5d Input means
6 Transmission part
7 Calculation part
8 Judgment part

The invention claimed is:

1. A prism prescription value acquisition system comprising:
a calculation part for numerically transforming a fixation disparity amount (unit: angle), which indicates a degree at which a visual axis is shifted from the central fovea of the retina when a subject conducts visual fixation of a target, into a prism prescription value by multiplying the fixation disparity amount by a coefficient when the fixation disparity amount is within ±4 minutes;
Herein, the prism prescription value is calculated according to the following equation:

$$AP_{ver}=k_{ver}*FD_{ver}$$

$$AP_{hor}=k_{hor}*FD_{hor}$$

$AP_{ver}$ represents a prism amount (unit: prism diopter) in a vertical direction (top and bottom direction) in the prism prescription value, $AP_{hor}$ represents a prism amount in a horizontal direction in the prism prescription value, and $FD_{ver}$ represents a fixation disparity amount in a vertical direction;

$FD_{hor}$ represents a fixation disparity amount in a horizontal direction, providing that each of coefficients $k_{hor}$ and $k_{ver}$ satisfies the following conditions:

$$0.3 \leq k_{ver} \leq 0.7$$

$$1.4 \leq k_{hor} \leq 2.0.$$

2. A prism prescription value acquisition system according to claim 1, further comprising a judgment part for judging whether a fixation disparity amount is within ±4 minutes or not, wherein when said judgment part judges that the fixation disparity amount is within ±4 minutes, said calculation part numerically transforms the fixation disparity amount into a prism prescription value.

3. A prism prescription value acquisition system according to claim 2, further comprising:

a measuring part for measuring a fixation disparity amount, and a transmission part for transmitting the fixation disparity amount measured by said measuring part to said calculation part;

said measuring part comprising a display means for displaying, after setting a direction of fixation disparity, a visual target for the right eye presented only to the right eye, a visual target for the left eye presented only to the left eye, and a visual target for visual fixation for which a subject conducts visual fixation, and an input means for flexibly moving at least either the visual target for the right eye or the visual target for the left eye displayed on said display means, wherein when the visual target for the right eye or the visual target for the left eye is moved, the visual target for visual fixation is not moved, and in a state in which a subject continuously conducts visual fixation of the visual target for visual fixation, a fixation disparity amount is measured from a shift amount of the two visual targets on said display means.

4. A prism prescription value acquisition system according to claim 3, wherein the visual target for the right eye (presented only to the right eye), the visual target for the left eye presented only to the left eye, and the visual target for visual fixation for which a subject conducts visual fixation displayed on said display means are included in one test figure, and said test figure can be flexibly placed at any location at a front of a background image provided with a plurality of visual targets for visual fixation.

5. A prism prescription value acquisition system according to claim 4, wherein said display means is a stereoscopic image display means capable of presenting different images to the right eye and the left eye separately; the visual target for the right eye is presented to the subject's right eye and the visual target for the left eye is presented to the subject's left eye.

6. A prism prescription value acquisition system according to claim 3, wherein said display means is a stereoscopic image display means capable of presenting different images to the right eye and the left eye separately; the visual target for the right eye is presented to the subject's right eye and the visual target for the left eye is presented to the subject's left eye.

7. A prism prescription value acquisition system according to claim 1, further comprising:

a measuring part for measuring a fixation disparity amount, and a transmission part for transmitting the fixation disparity amount measured by said measuring part to said calculation part;

said measuring part comprising a display means for displaying, after setting a direction of fixation disparity, a visual target for the right eye presented only to the right eye, a visual target for the left eye presented only to the left eye, and a visual target for visual fixation for which a subject conducts visual fixation, and an input means for flexibly moving at least either the visual target for the right eye or the visual target for the left eye displayed on said display means, wherein when the visual target for the right eye or the visual target for the left eye is moved, the visual target for visual fixation is not moved, and in a state in which a subject continuously conducts visual fixation of the visual target for visual fixation, a fixation disparity amount is measured from a shift amount of the two visual targets on said display means.

8. A prism prescription value acquisition system according to claim 7, wherein the visual target for the right eye (presented only to the right eye), the visual target for the left eye presented only to the left eye, and the visual target for visual fixation for which a subject conducts visual fixation displayed on said display means are included in one test figure, and said test figure can be flexibly placed at any location at a front of a background image provided with a plurality of visual targets for visual fixation.

9. A prism prescription value acquisition system according to claim 8, wherein said display means is a stereoscopic image display means capable of presenting different images to the right eye and the left eye separately; the visual target for the right eye is presented to the subject's right eye and the visual target for the left eye is presented to the subject's left eye.

10. A prism prescription value acquisition system according to claim 7, wherein said display means is a stereoscopic image display means capable of presenting different images to the right eye and the left eye separately; the visual target for the right eye is presented to the subject's right eye and the visual target for the left eye is presented to the subject's left eye.

11. A prism prescription value acquisition method for numerically transforming a fixation disparity amount (unit: angle), which indicates a degree at which a visual axis is shifted from the central fovea of the retina when a subject conducts visual fixation of a target, into a prism prescription value by multiplying the fixation disparity amount by a coefficient when the fixation disparity amount is within ±4 minutes;

Herein, the prism prescription value is calculated according to the following equation:

$$AP_{ver} = k_{ver} * FD_{ver}$$

$$AP_{hor} = k_{hor} * FD_{hor}$$

$AP_{ver}$ represents a prism amount (unit: prism diopter) in a vertical direction (top and bottom direction) in the prism prescription value, $AP_{hor}$ represents a prism amount in a horizontal direction in the prism prescription value, and $FD_{ver}$ represents a fixation disparity amount in a vertical direction;

$FD_{hor}$ represents a fixation disparity amount in a horizontal direction, providing that each of coefficients $k_{hor}$ and $k_{ver}$ satisfies the following conditions:

$$0.3 \leq k_{ver} \leq 0.7$$

$$1.4 \leq k_{hor} \leq 2.0.$$

12. A prism prescription value acquisition method according to claim 11, wherein whether a fixation disparity amount obtained by measurement A of the fixation disparity amount is equal to or less than a predetermined angle is judged, and when it is judged that the fixation disparity amount is equal to or less than a predetermined angle, the fixation disparity amount is numerically transformed into a prism prescription value, and when it is judged that the fixation disparity amount is more than a predetermined angle, the subject wears measurement spectacles provided with a predetermined prism amount suitable for the fixation disparity amount and measurement B of the fixation disparity amount is conducted again, then, any one of the following processes 1 to 3 is conducted;

(Process 1) When fixation disparity has ceased to be perceived in measurement B, the prism amount of the measurement spectacles is used as a prism prescription value;

(Process 2) When the subject still perceives fixation disparity even in measurement B and when in measurement B, eso fixation disparity is turned to exo fixation disparity or exo fixation disparity is turned to eso fixation disparity, any one of the following processes (i) to (iv) is conducted;

(i) In measurement A, when the subject doesn't wear measurement spectacles provided with a predetermined prism amount, half of prism value of the measurement spectacles in measurement B is used as a prism prescription value;

(ii) In measurement A, when the subject wears measurement spectacles provided with a predetermined prism amount, the average value of the prism amount of the measurement spectacles in measurement A and the prism amount of the measurement spectacles in measurement B is used as a prism prescription value;

(iii) In measurement A, when the subject doesn't wear measurement spectacles provided with a predetermined prism amount, prism prescription value is calculated by following formula $$AP = P2 - P2 \times FD2/(FD2 - FD1)$$

(iv) In measurement A, when the subject wears measurement spectacles provided with a predetermined prism amount, prism prescription value is calculated by following formula:

$$AP = P2 - (P2 - P1) \times FD2/(FD2 - FD1);$$

AP represents an amount of prism value (unit: prism diopter) of the aligning prism;

$$AP = P2 - (P2 - P1) * FD2/(FD2 - FD1);$$

AP represents a prism amount (unit: prism diopter) in the prism prescription value;

FD1 and FD2 are the fixation disparity amounts before and after eso fixation disparity has been turned to exo fixation disparity, or exo fixation disparity has been turned to eso fixation disparity in measurement B;

The sign of FD1 and FD2 is such that it is positive when the direction of fixation disparity is outward and negative when it is inward;

P1 and P2 are the prism amounts provided before and after eso fixation disparity has been turned to exo fixation disparity, or exo fixation disparity has been turned to eso fixation disparity in measurement B;

(Process 3) When the subject still perceives fixation disparity even in measurement B and when in measurement B, either eso fixation disparity or exo fixation disparity remains, the subject wears measurement spectacles provided with a higher power prism than the predetermined prism amount, and the fixation disparity amount is measured again, then the measurement of the fixation disparity amount is repeatedly conducted by increasing the power of the prism provided for the measurement spectacles until the state of (process 1) or (process 2) is achieved.

13. A prism prescription value acquisition apparatus comprising:

a calculation part for numerically transforming a fixation disparity amount (unit: angle), which indicates a degree at which a visual axis is shifted from the central fovea of the retina when a subject conducts visual fixation of a target, into a prism prescription value by multiplying the fixation disparity amount by a coefficient when the fixation disparity amount is within ±4 minutes;

Herein, the prism prescription value is calculated according to the following equation:

$$AP_{ver} = k_{ver} * FD_{ver}$$

$$AP_{hor} = k_{hor} * FD_{hor}$$

$AP_{ver}$ represents a prism amount (unit: prism diopter) in a vertical direction (top and bottom direction) in the prism prescription value, $AP_{hor}$ represents a prism amount in a horizontal direction in the prism prescription value, and $FD_{ver}$ represents a fixation disparity amount in a vertical direction;

$FD_{hor}$ represents a fixation disparity amount in a horizontal direction, providing that each of coefficients $k_{hor}$ and $k_{ver}$ satisfies the following conditions:

$$0.3 \leq k_{ver} \leq 0.7$$

$$0.4 \leq k_{hor} \leq 2.0.$$

14. A prism prescription value acquisition program for making a computer function as a calculation part for numerically transforming a fixation disparity amount (unit: angle), which indicates a degree at which a visual axis is shifted from the central fovea of the retina when a subject conducts visual fixation of a target, into a prism prescription value by multiplying the fixation disparity amount by a coefficient when the fixation disparity amount is within ±4 minutes;

Herein, the prism prescription value is calculated according to the following equation:

$$AP_{ver} = k_{ver} * FD_{ver}$$

$$AP_{hor} = k_{hor} * FD_{hor}$$

$AP_{ver}$ represents a prism amount (unit: prism diopter) in a vertical direction (top and bottom direction) in the prism prescription value, $AP_{hor}$ represents a prism amount in a horizontal direction in the prism prescription value, and $FD_{ver}$ represents a fixation disparity amount in a vertical direction;

$FD_{hor}$ represents a fixation disparity amount in a horizontal direction, providing that each of coefficients $k_{hor}$ and $k_{ver}$ satisfies the following conditions:

$$0.3 \leq k_{ver} \leq 0.7$$

$$1.4 \leq k_{hor} \leq 2.0.$$

* * * * *